US011471648B2

(12) United States Patent
Hulvershorn et al.

(10) Patent No.: US 11,471,648 B2
(45) Date of Patent: Oct. 18, 2022

(54) CATHETER INSERTION SYSTEM AND METHOD

(71) Applicant: Medline Industries, LP, Northfield, IL (US)

(72) Inventors: Justin Hulvershorn, Seattle, WA (US); Karl Schmidt, Seattle, WA (US); Shan Gaw, Seattle, WA (US); Matthew Lovell, Seattle, WA (US)

(73) Assignee: Medline Industries, LP, Northfield, IL (US)

( * ) Notice: Subject to any disclaimer, the term of this patent is extended or adjusted under 35 U.S.C. 154(b) by 694 days.

(21) Appl. No.: 15/571,168

(22) PCT Filed: Apr. 29, 2016

(86) PCT No.: PCT/US2016/030026
§ 371 (c)(1),
(2) Date: Nov. 1, 2017

(87) PCT Pub. No.: WO2016/178974
PCT Pub. Date: Nov. 10, 2016

(65) Prior Publication Data
US 2018/0133438 A1    May 17, 2018

Related U.S. Application Data

(60) Provisional application No. 62/155,881, filed on May 1, 2015.

(51) Int. Cl.
*A61M 25/01* (2006.01)
*A61M 25/06* (2006.01)
(Continued)

(52) U.S. Cl.
CPC .... *A61M 25/0113* (2013.01); *A61M 25/0097* (2013.01); *A61M 25/0606* (2013.01);
(Continued)

(58) Field of Classification Search
CPC ............ A61M 25/0606; A61M 25/06–25/065; A61M 25/0113; A61M 25/0097;
(Continued)

(56) References Cited

U.S. PATENT DOCUMENTS 3,312,220 A    4/1967 Eisenberg
5,312,359 A *  5/1994 Wallace ............ A61M 25/0631
                                                     604/164.08
(Continued)

FOREIGN PATENT DOCUMENTS

WO    2013124765 A1    8/2013
WO    2014074417 A2    5/2014
(Continued)

OTHER PUBLICATIONS

International Preliminary Report on Patentability and Written Opinion of the International Search Report dated Nov. 16, 2017 for PCT Application No. PCT/US2016/030026, 9 pgs.

*Primary Examiner* — Brandy S Lee
*Assistant Examiner* — Hong-Van N Trinh
(74) *Attorney, Agent, or Firm* — Fitch, Even, Tabin & Flannery LLP

(57) ABSTRACT

A catheter inserter including an actuator assembly to move a catheter assembly outside a housing by engaging the catheter assembly multiple times, in an example. The inserter includes a needle assembly in a housing that has a first position with a needle extending from the housing and a second position with the needle retracted into the housing. A catheter assembly is removably positioned in the housing and includes a catheter and a hub connected to the catheter. An actuator assembly is further mounted to the housing and operates to selectively engage a guidewire assembly to move
(Continued)

the guidewire past the needle and to selectively engage the catheter assembly to move the catheter and the hub outside the housing.

15 Claims, 27 Drawing Sheets

(51) Int. Cl.
  *A61M 25/00* (2006.01)
  *A61M 25/09* (2006.01)

(52) U.S. Cl.
  CPC .. *A61M 25/0631* (2013.01); *A61M 25/09041* (2013.01); *A61M 2025/0175* (2013.01); *A61M 2205/586* (2013.01)

(58) Field of Classification Search
  CPC .... A61M 25/09041; A61M 2025/0175; A61M 2205/586; A61M 25/0631
  See application file for complete search history.

(56) References Cited

U.S. PATENT DOCUMENTS

| | | |
|---|---|---|
| 5,409,461 A | 4/1995 | Steinman |
| 5,501,675 A | 3/1996 | Erskine |
| 6,695,814 B2 | 2/2004 | Greene et al. |
| 8,133,206 B2 | 3/2012 | Greene et al. |
| 8,382,721 B2 | 2/2013 | Woehr et al. |
| 8,647,301 B2 | 2/2014 | Bialecki et al. |
| 8,728,035 B2 | 5/2014 | Warring et al. |
| 8,774,907 B2 | 7/2014 | Rothenberg |
| 8,814,833 B2 | 8/2014 | Farrell et al. |
| 8,849,382 B2 | 9/2014 | Cox et al. |
| 2004/0116855 A1 | 6/2004 | Popov et al. |
| 2004/0267204 A1 | 12/2004 | Brustowicz |
| 2010/0094310 A1 | 4/2010 | Warring et al. |
| 2011/0282285 A1* | 11/2011 | Blanchard ......... A61M 25/0097 604/164.08 |
| 2011/0288482 A1* | 11/2011 | Farrell .............. A61M 25/0631 604/164.04 |
| 2012/0184910 A1 | 7/2012 | Woehr |

FOREIGN PATENT DOCUMENTS

| | | | | |
|---|---|---|---|---|
| WO | 2014133617 A1 | | 9/2014 | |
| WO | WO2014133617 | * | 9/2014 | |
| WO | WO-2014133617 A1 | * | 9/2014 | ........ A61M 25/0618 |

* cited by examiner

SECTION A-A

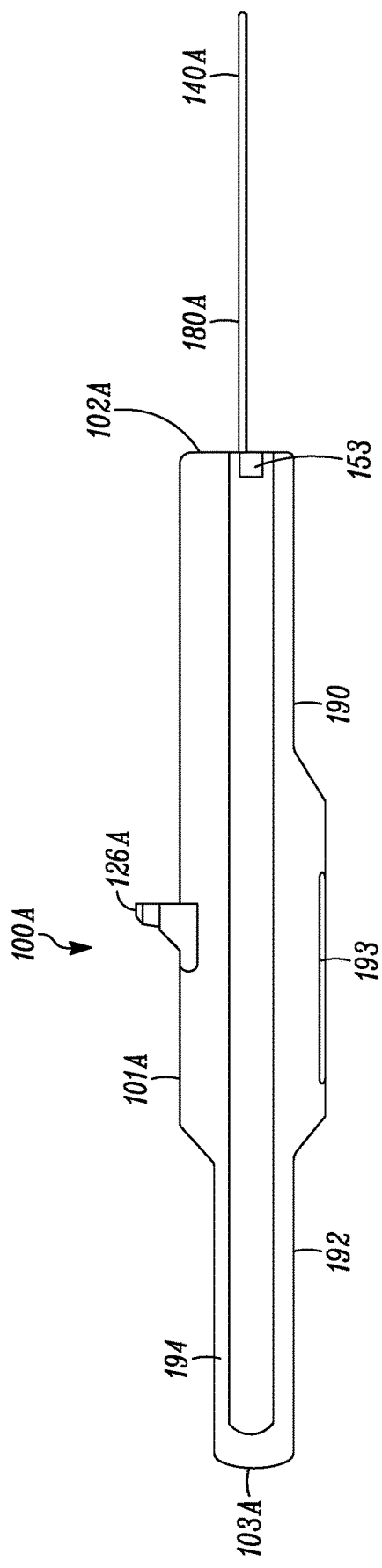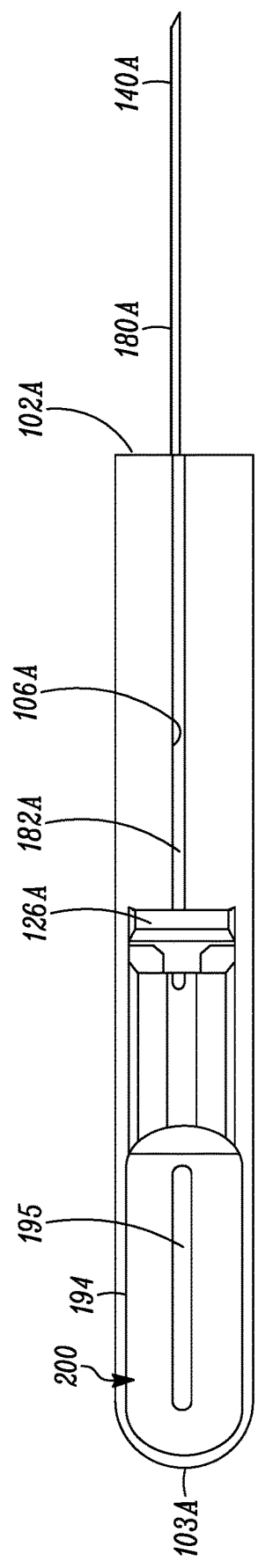
FIG. 15
FIG. 16

CATHETER INSERTION SYSTEM AND METHOD

CROSS-REFERENCE TO RELATED APPLICATION

This application is the U.S. national phase of PCT Application No. PCT/US2016/030026 filed Apr. 29, 2016 which claims the benefit of U.S. Provisional Application Ser. No. 62/155,881 filed May 1, 2015, the disclosures of which are incorporated in their entireties by reference herein.

TECHNICAL FIELD

The present disclosure relates to catheter insertion into a patient.

BACKGROUND

Vascular access catheters (e.g., central venous catheters ("CVCs"), peripherally inserted central catheters ("PICCs"), peripheral intravenous catheters ("PIVs"), sheaths, etc.) are used in many medical treatments. Some vascular access catheters come mounted on a needle ("over the needle" or "OTN" catheters). Some OTN catheters also include an integral guidewire. Ultrasound is commonly used during the insertion of vascular access catheters. The ultrasound can help with advancing the needle, the guidewire, and finally the catheter itself. Many OTN catheter insertion techniques require the use of two hands to insert the guidewire and/or catheter into the vasculature of a patient. In particular, catheters longer than about 1.5 inches typically require some type of two-handed insertion. One drawback of the two-handed techniques is that the ultrasound probe must be put down at some point during the insertion, and the loss of ultrasound visualization can lead to failure to successfully advance the guidewire and/or catheter. Also, two-handed techniques are technically more difficult, and require more skilled medical professionals to perform the insertion. Additionally, many existing catheter insertion techniques require the user to handle the catheter hub and/or the catheter shaft, which can contaminate the catheter and lead to catheter-related blood stream infections.

SUMMARY

A catheter inserter is described that can selectively engage the catheter to remove the catheter from the housing. The catheter inserter is configured to be held and operated with a single hand of the medical professional. In an example, the assembly can further selectively engage a guide wire to insert the guide wire through a needle into a vasculature of a patient. In an example, the needle can be retracted back into the housing. In an example, a needle safety device may be incorporated into the hub of the catheter or the catheter hub.

In an example, the catheter inserter includes a housing and a needle assembly in the housing. The housing can support a catheter assembly removably positioned in the housing. The catheter assembly can include a catheter and a catheter hub connected to the catheter. An actuator assembly is also supported on the housing to selectively engage the catheter assembly to advance the catheter and the catheter hub outside the housing. This example may not require a guide wire and may optionally include needle protection system.

In an example, the catheter inserter includes a housing and a needle assembly in the housing. The housing can support a guide wire assembly that can include a guide wire moveable relative to the housing and the needle. The housing can further support a catheter assembly removably positioned in the housing. The catheter assembly can include a catheter and a catheter hub connected to the catheter. An actuator assembly is also supported on the housing to selectively engage the guide wire assembly to move the guide wire past the needle and to selectively engage the catheter assembly to move the catheter and the catheter hub outside the housing.

In an example, the catheter inserter includes a housing and a needle assembly in the housing with a first position with a needle extending from the housing and a second position with the needle retracted into the housing. The housing can, optionally, support a guide wire assembly that can include a guide wire moveable relative to the housing and the needle. The housing can further support a catheter assembly removably positioned in the housing. The catheter assembly can include a catheter and a catheter hub connected to the catheter. An actuator assembly is also supported on the housing to selectively engage the guide wire assembly to move the guide wire past the needle. The actuator assembly can selectively engage the catheter assembly to move the catheter and the catheter hub outside the housing.

In an example, the housing and the actuator assembly are engagable by a single hand of a user. In operation, the user grips the housing with a single hand and uses a thumb or a finger to advance components into the vasculature of a patient. The actuator assembly selectively engages the catheter to advance the catheter from within the housing to outside the housing while having a distal end in the vasculature. The actuator assembly may engage the catheter a plurality of times as the travel distance of the catheter to be successfully engaged with a patient from the housing is greater than the range of motion of a digit of the user's hand that is engaged on the device. In the case of a guidewire, the actuator assembly may selectively engage the guidewire to extend the guidewire into the vasculature of the patient. Thereafter, the user may operate the actuator assembly to advance the catheter along the guidewire. In an embodiment, the actuator assembly may optionally engage the needle to retract the needle into the housing or otherwise cover the sharp end of the needle. These operational steps may be performed with a single hand of the user holding the housing and operating the actuator assembly.

In an example described herein, the actuator assembly includes a shuttle internal to the housing. The shuttle selectively engages the guide wire assembly and the catheter assembly to move either or both.

In an example described herein, a lock is supported by the housing to fix the needle assembly with the needle extending outside the housing for insertion into a patient and when needed, fix the needle in a retracted position in the housing. In an example, the lock can include a threaded locking ring on the outside of the housing that can threadedly engage housing to fix the needle in the extended position or the retracted position. Other releasing structure can be used to retract the needle into the housing. Other structures move the needle protector to the end of the needle. In an example, the protecting cover for the needle travels with the catheter to catheter hub. The protecting cover can be released at the end of the needle to cover the sharp end. The protecting cover may automatically be released as the needle sharp end.

In the examples described herein, the housing and the actuator assembly are engagable by a single hand of a user.

In an example, material is removed from the patient facing side of the distal end of the housing to allow a narrow insertion angle.

In an example, the user is able to advance the guidewire and/or catheter without physical handling either the guidewire and/or the catheter.

In an example, the catheter assembly includes a hub, with an actuator connected to hub. The hub engages a latch mechanism to open the housing to allow the catheter assembly to move outside the housing.

In an example, the housing includes a door assembly that is openable upon movement of the actuator assembly.

In an example, the door assembly includes at least one door held in a closed position by the latch mechanism.

In an example, the door includes a latch, wherein the latch mechanism includes a control arm with a catch to receive the latch. The control arm is moved to release the latch from the catch with the hub engaging the arm.

In an example, the door assembly includes at least two doors that matingly engage when closed and support the needle assembly at the distal end of the housing when closed.

In an example, the two doors form an aperture through which a needle of the needle assembly and a catheter of the catheter assembly extend with the doors in the closed position.

In an example, the catheter extends from the hub and a free end of the catheter is fenestrated.

In an example, the fenestrated free end of the catheter includes at least three apertures spaced around the end so that at least some of a fluid inserted into a patient through the catheter is stabilized by the fluid flowing out the apertures as well as the open end of the catheter.

BRIEF DESCRIPTION OF THE DRAWINGS

FIG. 15 shows a side elevational view of a catheter inserter in an example embodiment.

FIG. 16 shows a side elevational view of a catheter inserter in an example embodiment.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

The present disclosure describes catheter inserters 100, 100A, which can be used with a single hand by the medical professional. In some examples, the catheter inserter has a guidewire. However, the guidewire may not be required for all examples. The catheter inserter allows the needle to be fixed to a housing and allows the catheter, e.g., with a hub, to be releasably mounted in the housing. The catheter can be slid out of the housing through operation of an actuator, either with multiple linear movements or a single linear movement. The actuator may also operate to secure the sharp end of the needle, e.g., by covering the needle end with a protection cover.

Figure 1:
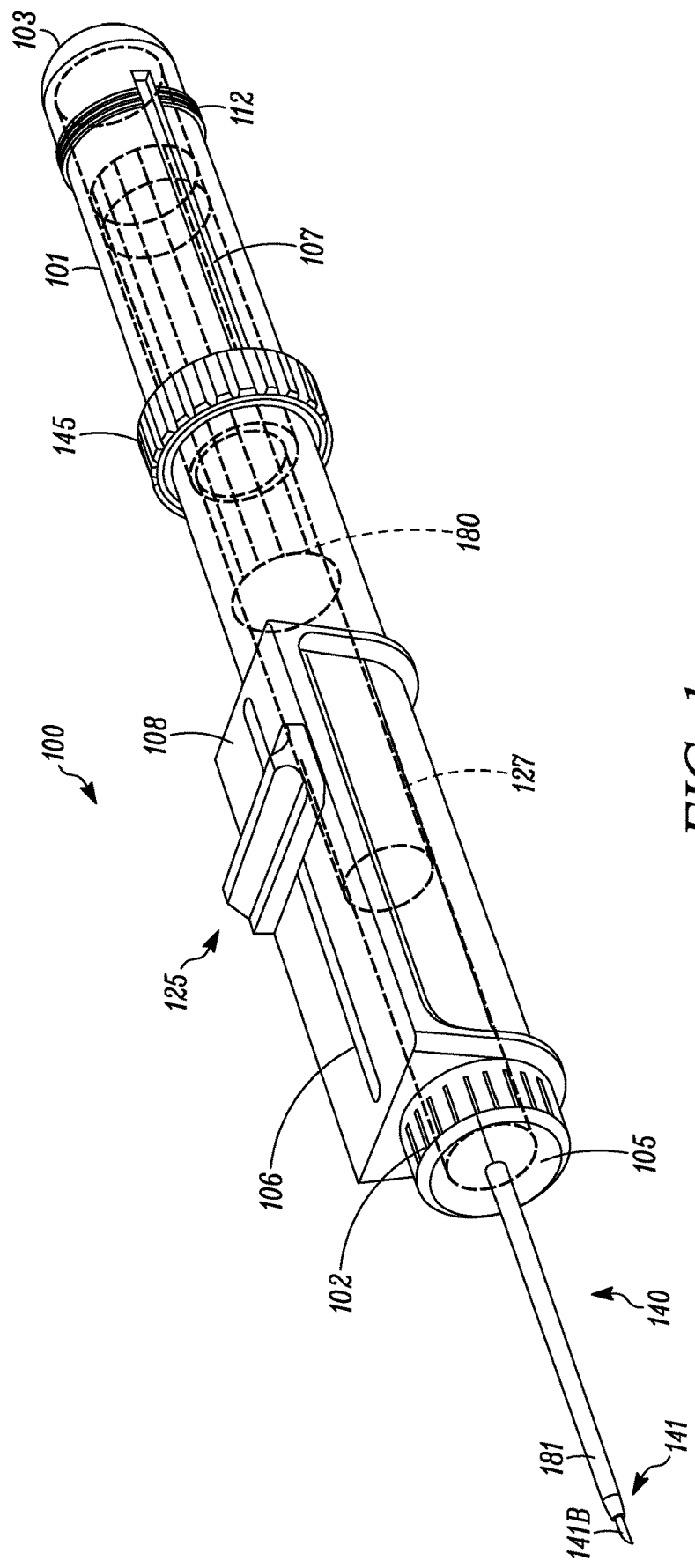
FIG. 1 is a perspective view of a catheter inserter in an example embodiment.
Figure 2:
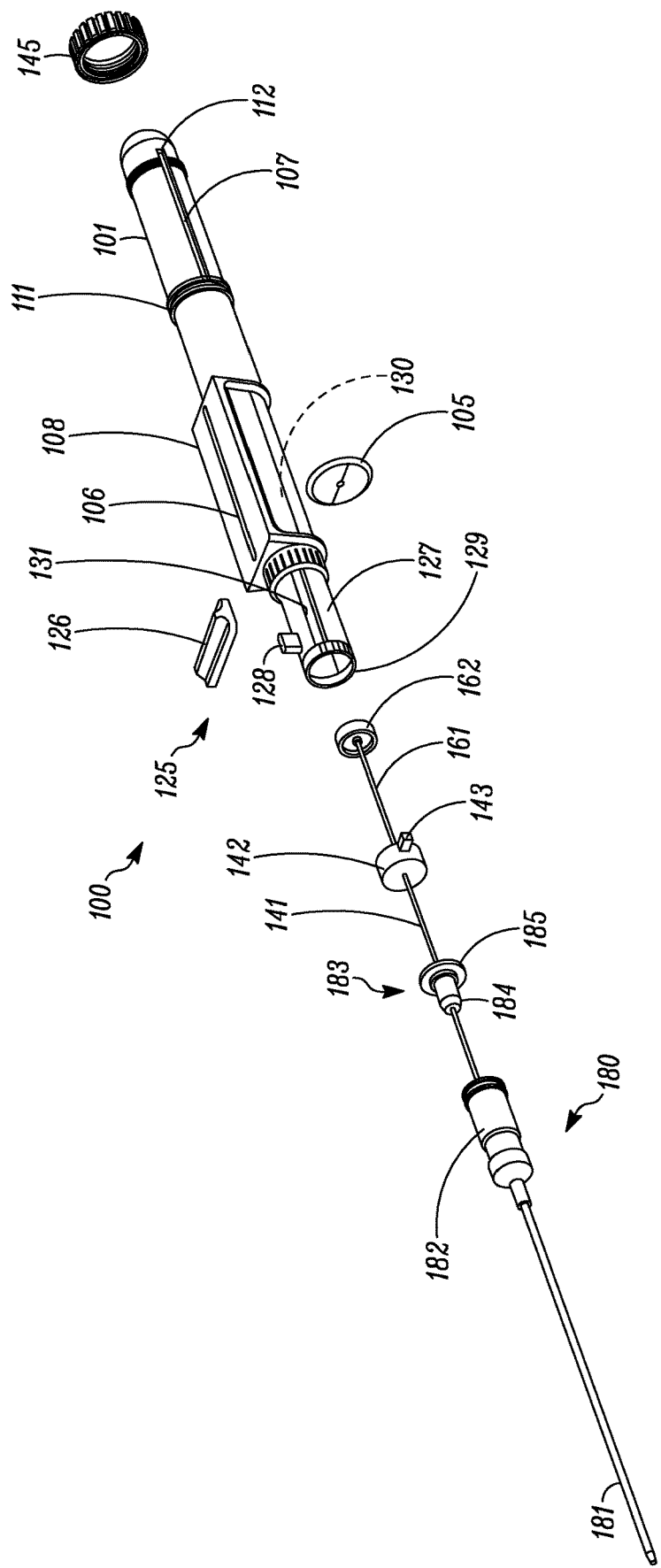
FIG. 2 is an exploded view of the catheter inserter in an example embodiment.

With reference to FIG. 1 and FIG. 2, they show a catheter inserter 100 that operates to insert a catheter into the body of a patient, e.g., a human or animal. Catheter inserter 100 includes a housing 101 that is elongate and cylindrical between a distal end 102 and a proximal end 103. The housing 101 may have other shapes, but must include an at least partly hollow interior sized to moveably receive a catheter assembly. The proximal end 103 can be closed and integrally formed with the elongate, hollow body of the housing. The distal end 102 is open so that various components can extend outside the housing. A seal 105 is positioned on the distal end 102. The seal 105 can be frangible, in an example, to allow components to be pressed therethrough. The seal 105 may include a slit extending along a diameter that allows small components to extend therethrough but not allow larger objects therethrough. Such larger objects may force the seal 105 off the distal end 102. The housing 101 may be other shapes that are elongate and have an open interior to receive other components. The housing 101 can be formed of a rigid polymer and portions thereof may be transparent. With the housing 101 being transparent, the internal components in the housing 101 of the catheter inserter 100 can be viewed while operating. The housing 101 is adapted to support an actuator assembly 125 that selectively engages a guide wire assembly 160 and a catheter assembly 180 to move these assemblies relative to the housing. The housing 101 further supports a needle assembly 140 in a fixed position to insert into the patient's body and a retracted position after the catheter is inserted into the patient's body. The housing 101 includes a slot 106 adjacent the distal end 102 that aligns with the actuator assembly 125 and allows the actuator assembly to be inside and outside the housing. A slot 107 is adjacent the proximal end 103 and allows the needle assembly 140 to be both inside and outside the housing 101. A platform 108 is provided on the housing or integrally formed with the body of the housing 101. Threads 111 and 112 are respectively positioned at each end of the slot 107. In a use case, the catheter inserter 100 can be used with one hand of the medical professional. The other hand of the medical professional can be free to engage the patient or perform other tasks, e.g. holding an ultrasound probe.

The actuator assembly 125 includes an actuator 126 that is adapted to slide on or in alignment with a top surface of the platform 108 or the housing. In an example, the actuator 126 has a width that is essentially the same as or slightly less than the width of the top surface of the platform 108. Actuator 126 can include at least one upraised ridge extending away from the housing 101 and providing an engagement surface for a user's thumb or finger. Actuator 126 further includes a recess (not shown) in the bottom thereof. Actuator assembly 125 further includes a shuttle 127 with an outer diameter less than an inner diameter of the housing to allow the shuttle to travel in the longitudinal direction in the housing 101. The shuttle 127 includes a protuberance 128 that extends upwardly from the body of the shuttle through the slot 106 to be fixedly received in the recess of the actuator 126 when assembled (FIG. 1). The protuberance 128 is positioned closer to the shuttle distal end 129 than the shuttle proximal end 130. A user can engage the actuator 126 and move the shuttle 127 proximally and distally along the length of the slot 106.

Housing and shuttle 127 can have an elongate slot 131 to provide visual access into the interior of the housing 101. The internal components, e.g., the actuator assembly internal parts, the catheter, the needle, etc., can be viewed through the slot 131. The slot 131 also reduces weight and provides a contact portion for the user's hand to grip and guide the housing.

The needle assembly 140 includes a needle 141 with a distal, sharp end to insert into a patient and a proximal end that is fixed to a base 142. The base 142 can be shaped to match the interior of the housing 101 to allow the needle assembly 140 to travel in the housing. In an example, the base 142 is generally cylindrical with a protuberance 143 extending outwardly. The protuberance 143 is sized to extend outwardly through the slot 107, thus, the needle assembly can travel longitudinally in the housing 101 along the length of the slot 107. The protuberance and slots further align the needle's bevel tip so that the beveled tip is at the same location. That is, the needle (and other components) do not rotate within the housing interior. However, a moving needle may be desirable when storing the catheter inserter 100 or after using the assembly 100, it is not typically desired during use. A locking ring 145 is provided to fix the needle assembly 140 in a use position with the distal end of the needle 140 extended outside the housing and fixed in position. The locking ring 145 can further fix the needle assembly in a retracted, non-use position with the distal end of the needle 140 retracted into the housing 101. The locking ring 145 can removably engage the housing 101 at either threads 111 or threads 112. While described as threads other releasable engagements can be used to fix the locking ring in place on the housing to fix the needle assembly in position. A pawl and/or a detent are examples that can be used. In an example, the locking ring 145 has an internal channel that engages the protuberance 143 such that the locking ring can be disengaged from housing moved to the a new position and reengaged to the housing at a second position. This allows the needle to either be extended from the housing distal end 103 or retracted into the housing 101. Locking structures that can selectively lock the needle assembly are within the scope of the present disclosure.

In an alternative example, the needle assembly protuberance 143 extends outside the slot 107 and the needle assembly is urged by a mechanical means, e.g., a spring, into a retracted position. The slot 107 can be configured to allow the protuberance 143 to travel distally and be locked in a forward position with the needle extended from the housing 101. The slot 107 can be non-linear to allow the protuberance 143 to travel at an angle relative to elongate portion of the slot 107 and lock the protuberance 143 in place. The slot 107 can have a keyhole at the distal end to fix the needle assembly 140 in the distal (forward or leftward in FIGS. 1-8) position.

The guide wire assembly 160 (see FIG. 2) includes a guide wire 161 that is sized to extend through the interior of the needle 141 to extend into a vein or an artery of a patient. The guide wire 161 is adapted to further guide and lead the catheter into the vein or artery. A base 162 is fixed to a distal end of the guide wire 161. The base 162 can be a short cylinder or have a generally cylindrical shape to match the interior of the housing 101. The base 162 is adapted to be selectively engaged by the shuttle 127 to move the guide wire 161 out of the distal end of the needle 141. When assembled, the base 162 is positioned proximally relative to the needle base 142. In an example, the needle base 142 may have a recess (not shown) to receive the guide wire base 162 therein when the guide wire assembly 160 is moved distally by the shuttle or when the needle assembly is retracted into the housing 101.

The catheter assembly 180 includes a catheter 181 fixed to a catheter hub 182. The catheter hub 182 is sized to fit within the interior of the housing 101 and to travel out of the distal end 102. Catheter hub 182 includes various fittings and/or ports that allow other medical devices to be connected to the catheter hub 182 or allow access to the patient through the catheter 181. A distal end of the catheter 181 may be fenestrated with fenestra 186. The fenestra 186 may be uniformly spaced around the catheter. There may be multiple rings of fenestra. The fenestra 186 can operate as ports that allow fluid to exit the catheter radially outwardly to stabilize the end of the catheter, e.g., when high pressure fluid is forced into the catheter. This will reduce the contact of the catheter against the vasculature.

Catheter assembly 180 can include a cap 183 that is sized to travel within the interior of the housing 101. The cap 183 includes a crown 184 sized to be received within the interior of the catheter hub 182. The cap 183 includes a brim 185 at a proximal end of the crown 184. The brim 185 has a greater diameter than the crown 184. In an example, the brim 185 has an outer diameter that is smaller than the inner diameter of the interior of the housing and slightly greater than the largest diameter of the catheter hub 182. The cap 183 is adapted to be engaged by the shuttle 127 to move the catheter assembly 180 from a fully retracted position in the housing 101 through the distal end 102 to a fully extended position with the catheter 181 and catheter hub 182 free from the housing 101. In an example, the seal 105 is pressed off the housing distal end 103 by the catheter hub 182. In another example, the seal 105 is flexible to allow the catheter 181 and catheter hub 182 to pass therethrough without being removed from the housing distal end 102.

Referring now to the use cases of the catheter inserter 100 as shown in FIGS. 1 and 3-8, the initial position of the catheter inserter 100 for use is shown in FIG. 1 with the needle 141 extending from the housing distal end 102 through the seal 105. The actuator assembly 125 is shown in its initial position with the actuator 126 being positioned more proximally than distally along the slot 106 on the platform 108. Thus, the shuttle 127 is in an initial position intermediate within the housing. The needle assembly 140 is held in its forward, extended position by the locking ring 145 being engaged at the distal end of slot 107. This fixes the needle end 141B in its forward position. A user grips then housing 101, e.g., with the users thumb on the platform 108 or near actuator 126, insert the needle 141 into the patient's vein or artery.

Figure 3:
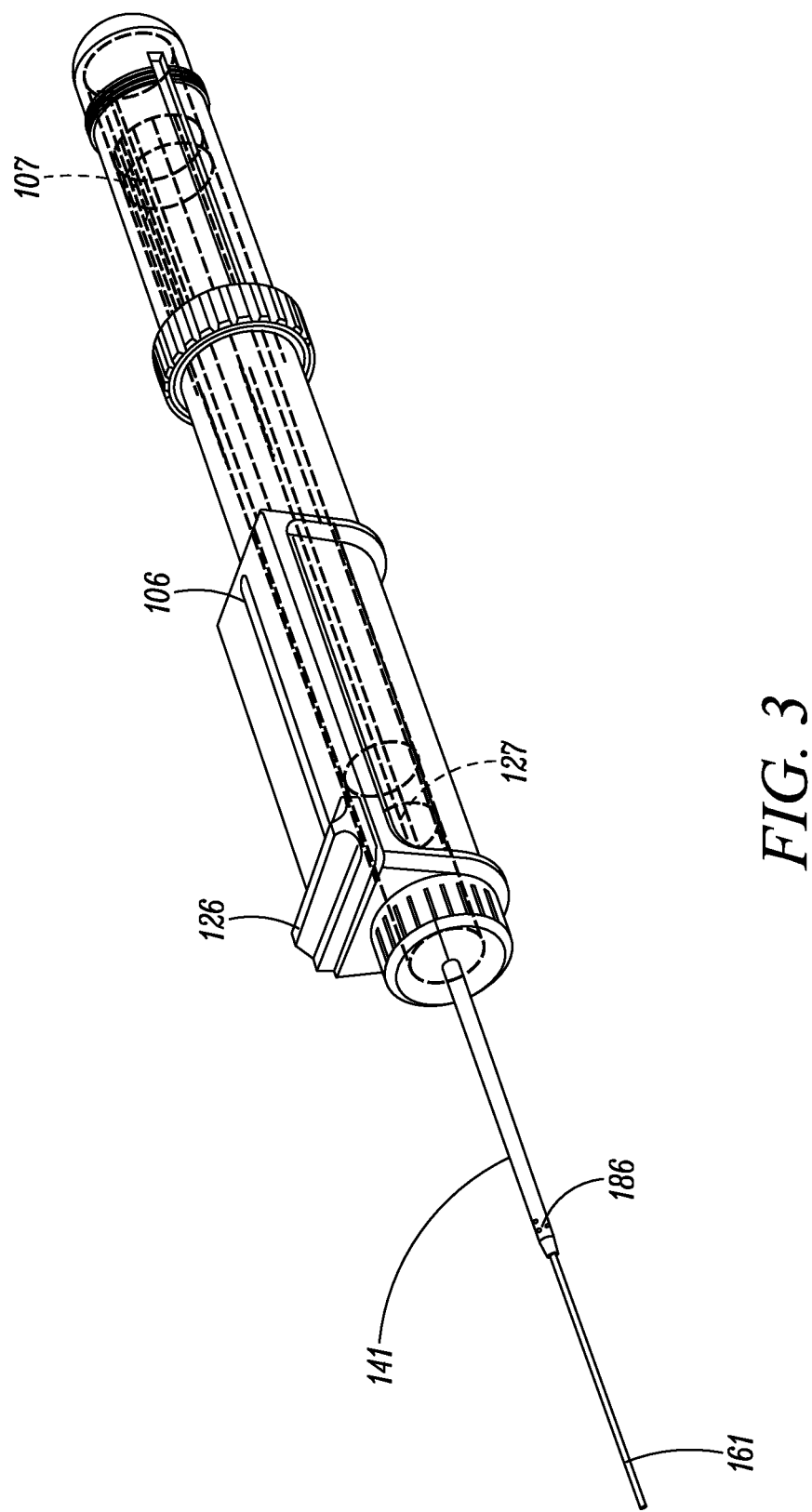
FIG. 3 is a perspective view of the catheter inserter in an example embodiment.

FIG. 3 shows the catheter inserter 100 after the needle 141 is inserted into the patient (not show) and the guide wire 161 extends distally out of the needle end 141B. In operation the user engages the actuator 126, e.g., with the same hand (e.g., with a thumb or the index finger) as used to insert the needle into the patient, and press the actuator 126 forward along the slot 106. The shuttle 127, which is fixed to the actuator 126, moves forward and is engaged with the guide wire base 162. Thus, the shuttle 127 moves the guide wire base 162 and guide wire 161 distally. The guide wire 161 extends out of the needle end 141B. The forward movement will end when either the protuberance 128 contacts the distal end of the slot 106 or the guide wire base 162 contacts the needle base 142. At this time the shuttle 126 releases the guide wire base 162. The guide wire 161 will be held in place by friction between the wire 161 and patient's body or between the wire 161 and needle 141.

Figure 4:
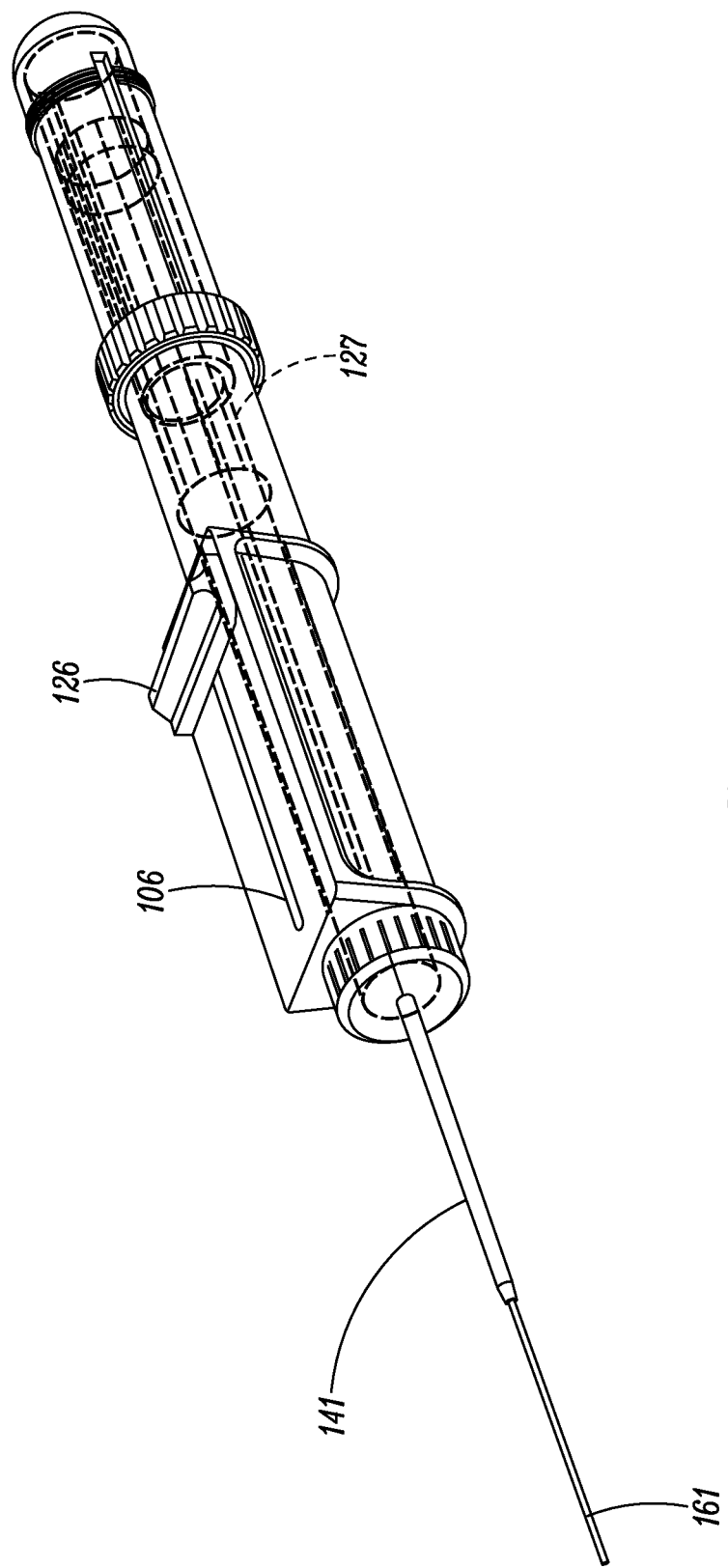
FIG. 4 is a perspective view of the catheter inserter in an example embodiment.

FIG. 4 shows the catheter inserter 100 after the shuttle 126 releases the guide wire assembly 160 and the actuator 126 is retracted proximally to the proximal end of the slot 106. In an example, the actuator 126 moves past the initial position shown in FIG. 1. The shuttle 127 now engages the catheter assembly 180. In an example, a rear part of the shuttle 127 engages the catheter assembly 180. In an example, the shuttle engages the cap 183. The catheter 181 in now ready to move forward.

Figure 5:
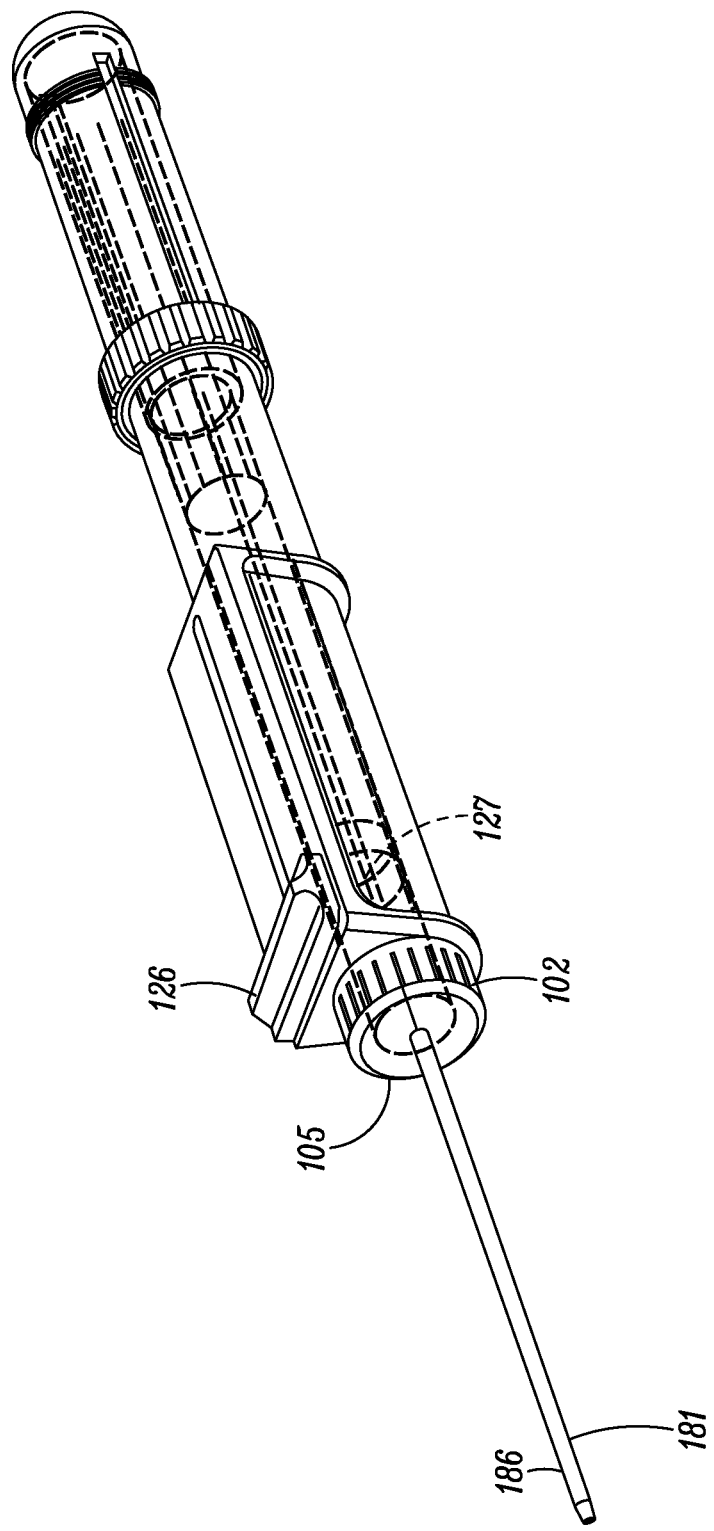
FIG. 5 is a perspective view of the catheter inserter in an example embodiment.

FIG. 5 shows actuator 126 moved again to the forward position by a user, which causes the shuttle 127 to move distally and the engaged catheter assembly 180 to move distally. The catheter 181 extends out of the housing distal end 102 and over the needle 141 and guide wire 161. In an example, the catheter 181 extends through the center of the seal 105. The catheter 181, guide wire 161 and needle 141 are all within the vein (or artery) of the patient.

Figure 6:
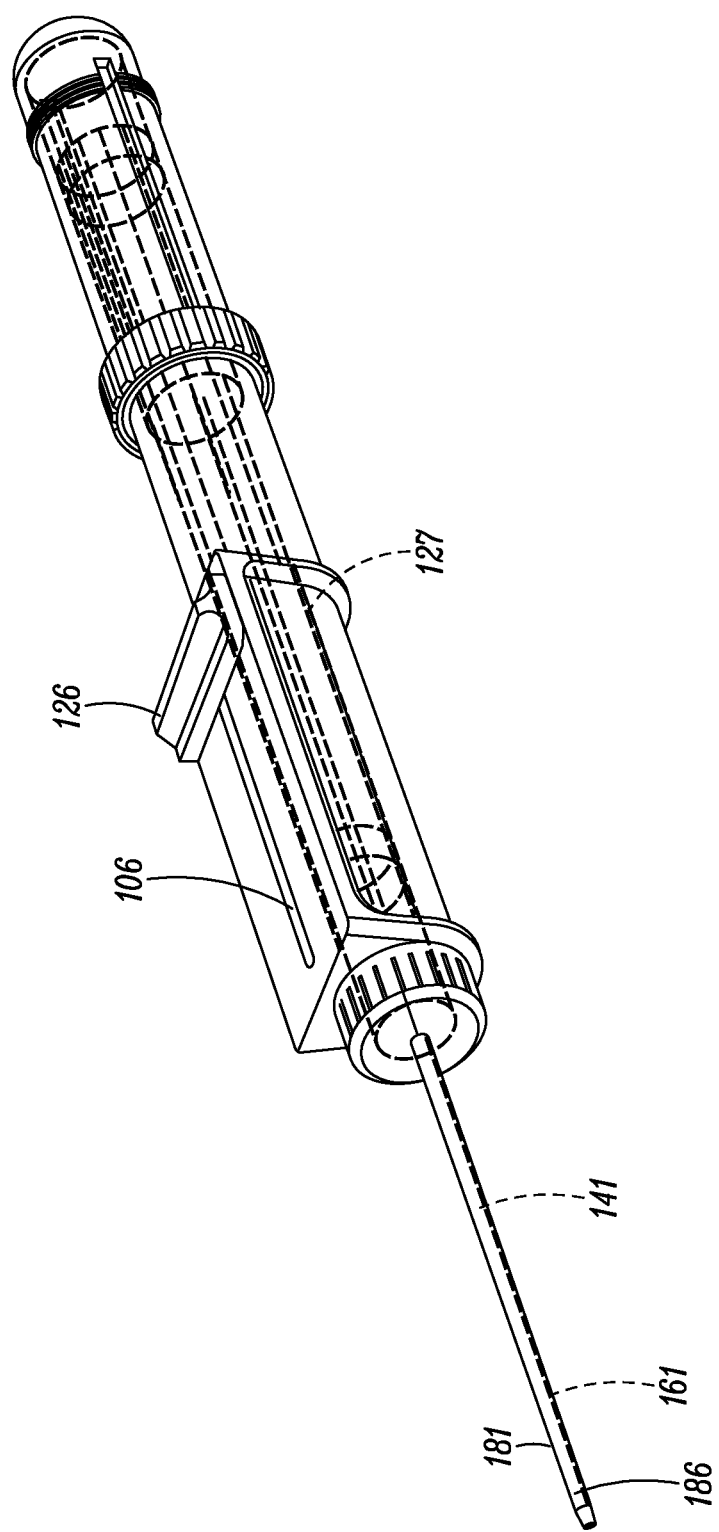
FIG. 6 is a perspective view of the catheter inserter in an example embodiment.

FIG. 6 shows the actuator 126 moved to a proximal position whereat the shuttle 127 again engages the catheter assembly 180. The shuttle 126 may engage the catheter assembly 180 with a more distal (forward) portion of the shuttle than done in FIG. 5. This allows the shuttle 127 to use a same travel path (substantially similar distance) to move the catheter assembly 180 a distance greater than the travel path of the shuttle 127. The maximum travel distance of the shuttle 127 is the length of the slot 106.

Figure 7:
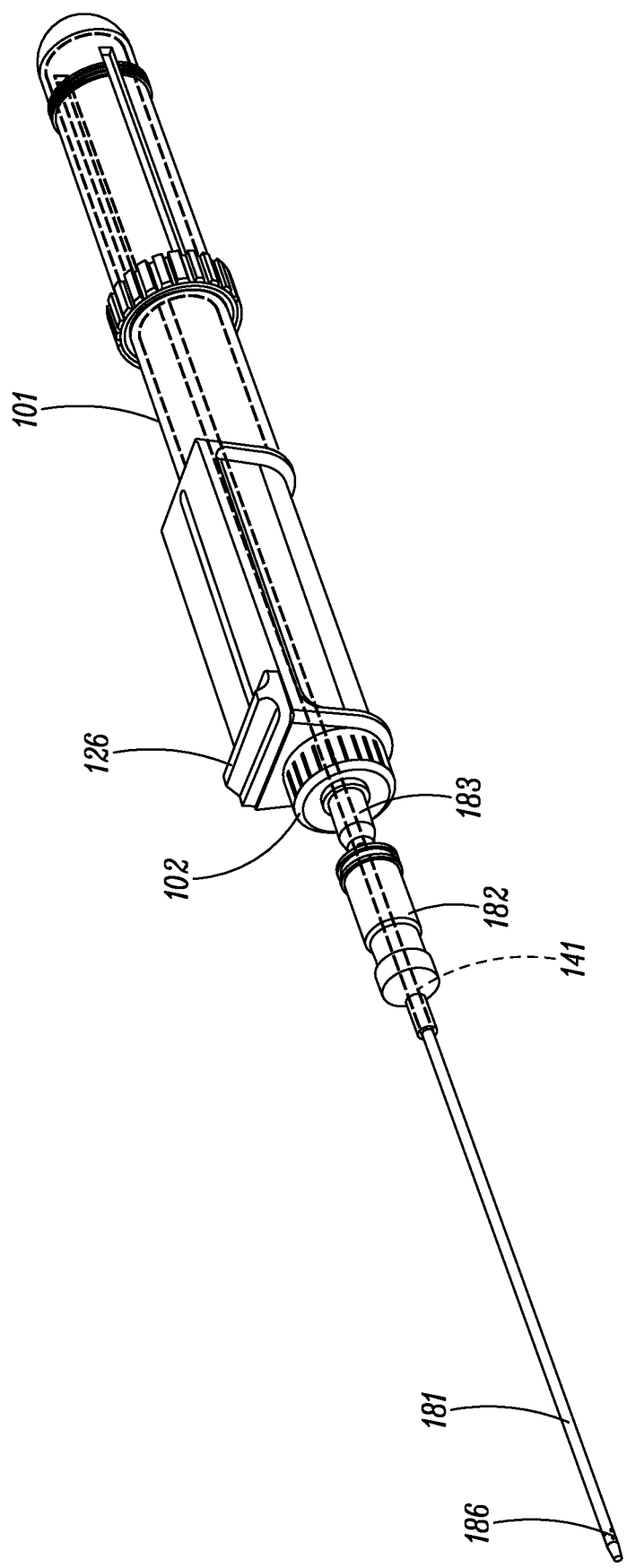
FIG. 7 is a perspective view of the catheter inserter in an example embodiment.

FIG. 7 shows the release of the catheter assembly 180 from the housing 101. To achieve this release, the user moves the actuator 126 to the distal position with the shuttle being again engaged with the catheter assembly 180. Here a front part of the shuttle 127 engages the catheter assembly, e.g., the cap 183. The actuator 126 is moved forward along the slot 106 to move the shuttle 127 forward. The shuttle 127 forces the catheter 181 and catheter hub 182 beyond the housing distal end 102. The cap 183 is caught at the housing distal end 103, e.g., by at least one radially inwardly extending finger(s).

Figure 8:
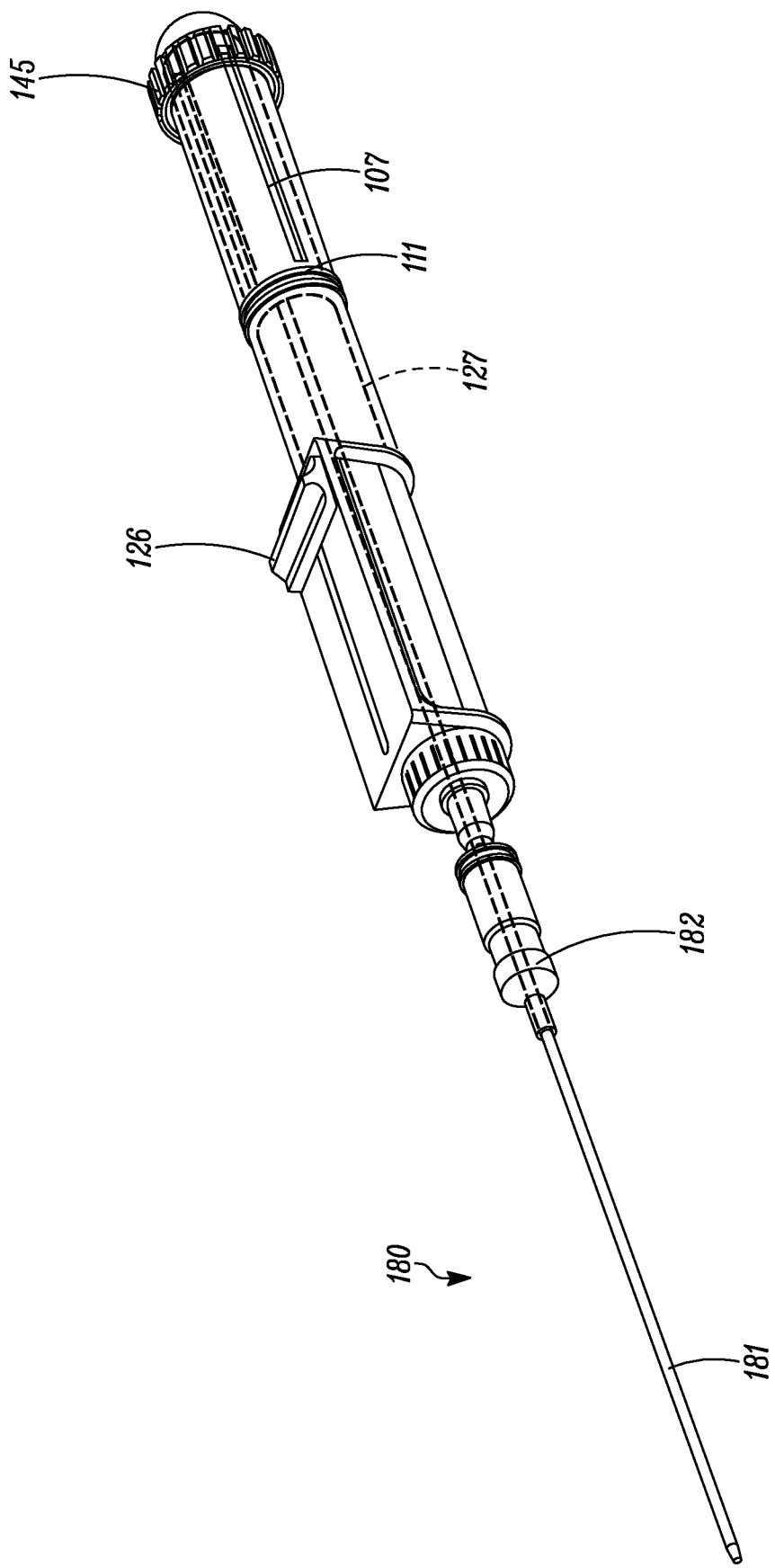
FIG. 8 is a perspective view of the catheter inserter in an example embodiment.

FIG. 8 shows the end position of the catheter inserter 100 with the actuator 126 and shuttle 127 retracted proximally in the housing 101. The locking ring 145 has been released from the forward threads 111 and now engaged on the proximal threads 112. Moving the locking ring 145 proximally retracts the needle 141 into the housing 101. When the needle base 142 is larger than the guide wire base 162, the guide wire 161 is retracted with the needle by moving the locking ring 145. Retracting the needle 141 into the housing can be done before completely withdrawing the needle 141 and guide wire 161 from the catheter 181. This keeps the needle covered for most of the process to assist with safety.

In an example, the housing proximal end 103 includes a receptacle sized to at least partially receive the wire guide base 162 and possibly the needle base 142 as well.

As shown in FIGS. 1-8, the housing distal end 102 includes a plurality of individual fingers that longitudinally aligned with the main body of the housing so that the inner shape, e.g., diameter is the same as the rest of the main body of the housing 101. The fingers may be cantilevered from the main body. The free ends of the fingers extend slightly inwardly. In an example, the free ends can move radially outwardly against their at rest position to allow components to be moved within the housing 101 during assembly. The free ends of the fingers may engage the seal 105 to removably fix the seal 105 to the housing distal end 102. The free ends of the fingers may further allow the catheter hub 182 to pass thereby by engage the brim 185 of the cap 183 to keep the cap within the housing 101. The crown 184 of the cap 183 is sized to extend through the open center defined by the free ends of the fingers.

With reference to FIGS. 9A-9G and FIGS. 10A-10G, these figures with like suffixes show the catheter assembly in a same position of use. FIGS. 9A-9G show a plan view to illustrate the position of the actuator and other external components. FIGS. 10A-10G are cross sectional views taken along cross sectional lines on corresponding FIGS. 9A-9G (corresponding figures have the same suffix). FIGS. 10A-10G illustrate the internal components in greater detail than the plan views of FIGS. 9A-9G. FIGS. 10A-10G show cross-sectional views of the catheter inserter in respective operational positions that correspond to views FIGS. 9A-9G.

Figure 9A:
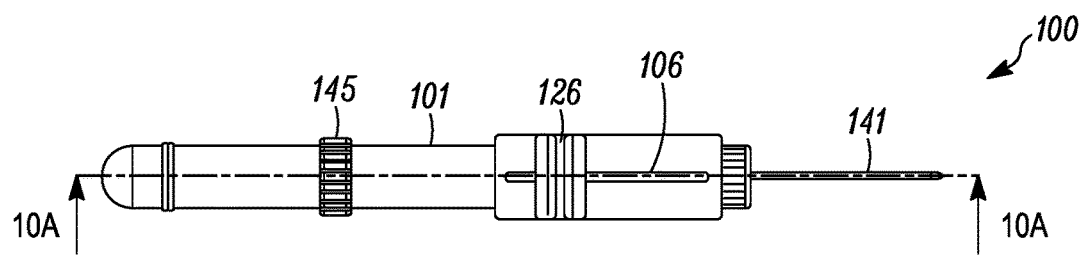
FIGS. 9A-9G show plan views of the catheter inserter in respective operational positions in an example embodiment.
Figure 10A:
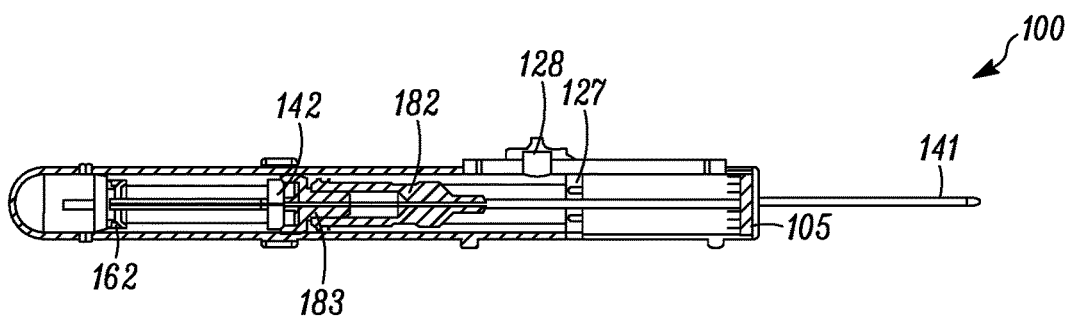
FIGS. 10A-10G show cross-sectional views of the catheter inserter in respective operational positions in an example embodiment.

An initial position of the catheter inserter 100 is shown in FIGS. 9A and 10A. The actuator 126 is fixed to shuttle 127. The shuttle 127 has three positions (e.g., proximal, middle, distal) that engage with the guide wire assembly 160 and catheter carrier 180. Following insertion of the needle 141 into the vasculature (e.g., venipuncture), the actuator 126 is slid forward, with the shuttle 127 being engaged to the guide wire assembly 160, to advance the proximal end of the guide wire 161. The guide wire 161 extends out of the end of the needle 141. In an example, a rear part of the shuttle 127 engages the base 162 to move the guide wire forward. In an example, the actuator 126 can travel in the slot 106 in the housing (e.g., a handle), e.g., greater than about 0.5 inch, up to 1.0 inch or up to about 1.5 inches.

Figure 9B:
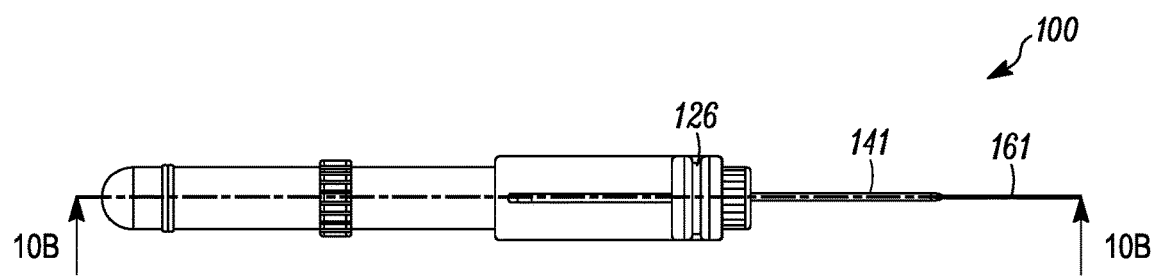
Figure 10B:
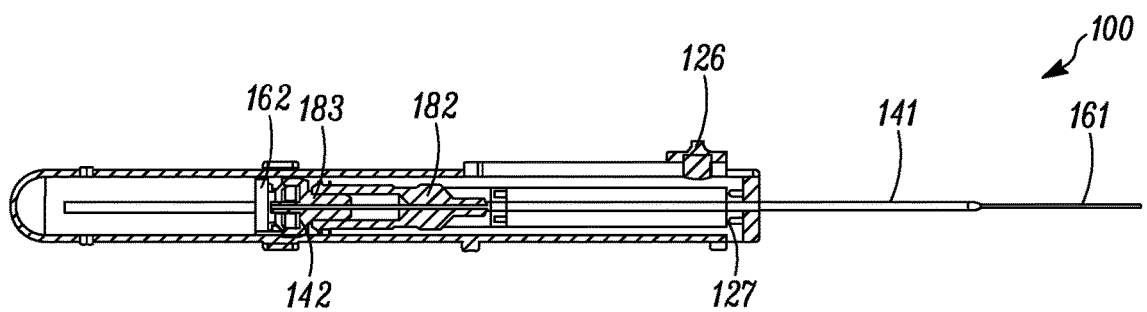

A subsequent position of the catheter inserter 100 is shown in FIGS. 9B and 10B. The guide wire assembly 160 engages the back end of the needle assembly 140 in its fully extended position. In an example, the guide wire assembly 160 locks into the back end of the needle assembly 140. The actuator 126 slides back the length of the slot in the housing, leaving in place the guide wire assembly 160 and the needle assembly 140. That is, the shuttle 127 disengages from the guide wire assembly 160 and the needle assembly 140, if engaged.

Figure 9C:
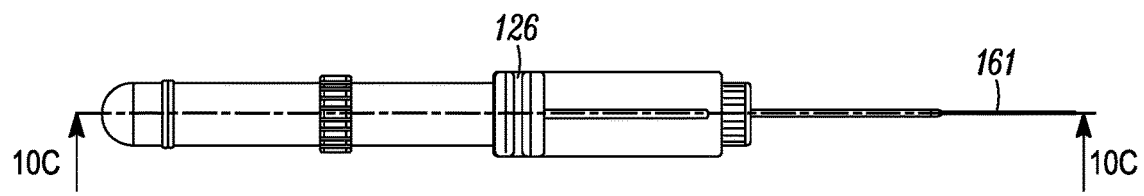
Figure 10C:
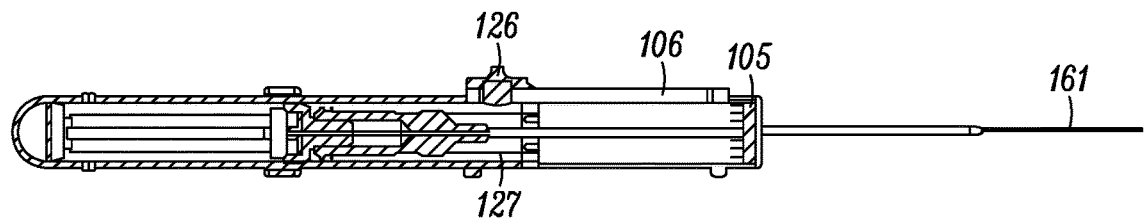

Another position of the catheter inserter 100 is shown in FIGS. 9C and 10C. Once the actuator 126 slides back, the middle part/position of the shuttle 127 engages with the catheter carrier 180. The actuator 126 is slid forward, moving the shuttle 127 forward to insert the catheter 181 past the end of the guide wire 161. In an example, the catheter 181 travels past the guide wire 161 by a length of greater than 0.25 inch to 2.0 inches, or 0.5 inch to approx. 1.5 inch.

Figure 9D:
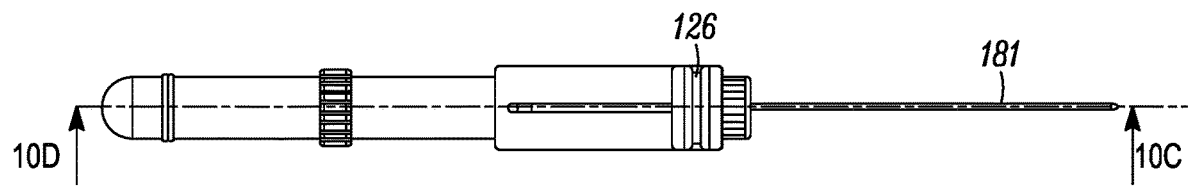
Figure 10D:
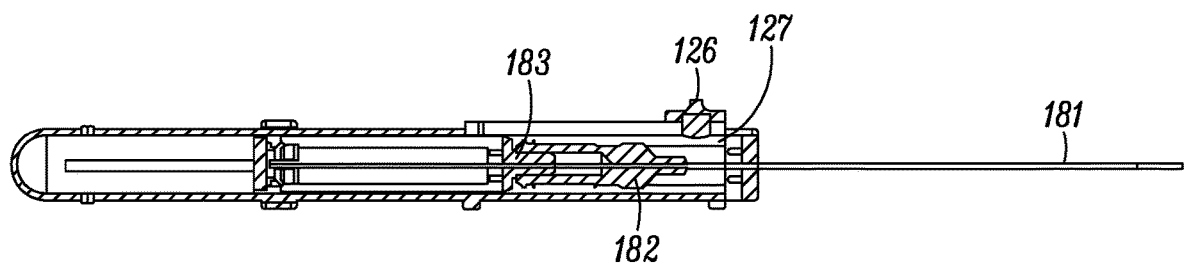

Another position of the catheter inserter 100 is shown in FIGS. 9D and 10D. The actuator 126 is slid back again, after disengaging from the catheter assembly 180 to leave the catheter assembly in place. Actuator 126 travels back the full length of the slot 106 in the housing 101 to re-engage the catheter assembly 180 with a front part of the shuttle 127.

Figure 9E:
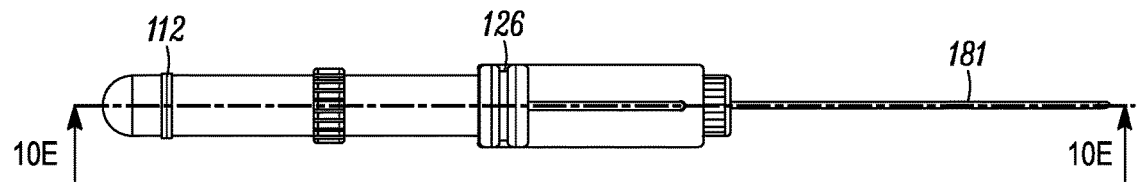
Figure 10E:
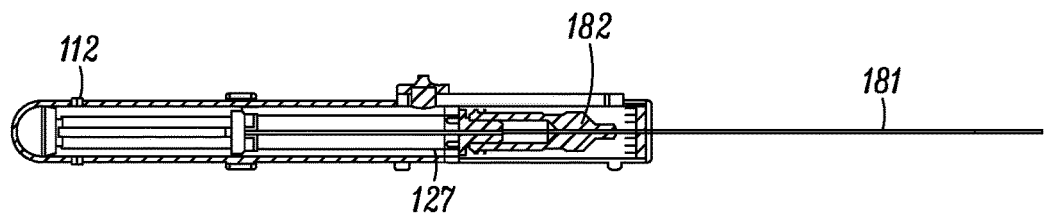

Another position of the catheter inserter 100 is shown in FIGS. 9E and 10E. A front part of shuttle 127 engages a rear part of the catheter assembly 180. Actuator 126 is now slid forward to further advance the catheter assembly 180 until the catheter hub 182 exits the distal end 102 of the housing 101.

Figure 9F:
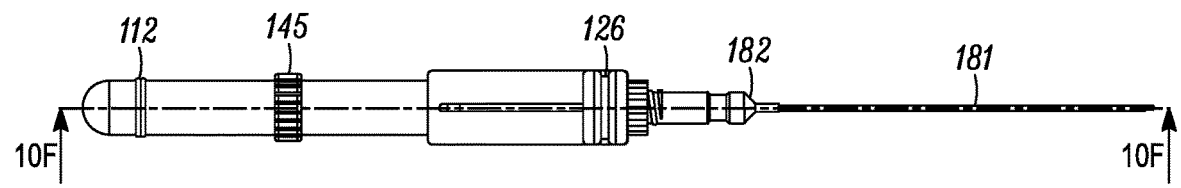
Figure 10F:
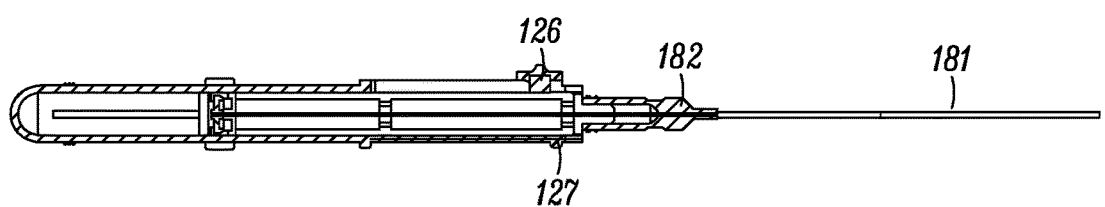

Another position of the catheter inserter 100 is shown in FIGS. 9F and 10F. Once catheter 181 and catheter hub 182 exit the housing 101, a lock 145 is used to fix the needle assembly 140 in place relative to the housing 101. The lock can engage the housing and the needle assembly to fix the needle assembly in at least two positions, e.g., with the needle retracted into the housing and with the needle extended. In an example, the lock is a locking ring that can be unscrewed from the distal threads 111 to free the needle assembly 140 so that it can slide back into the housing 101. Another locking mechanism that fixes the needle in the extended position and the retracted position may be used.

Figure 9G:
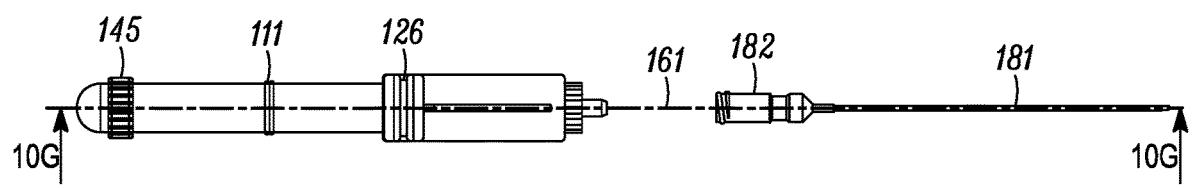
Figure 10G:
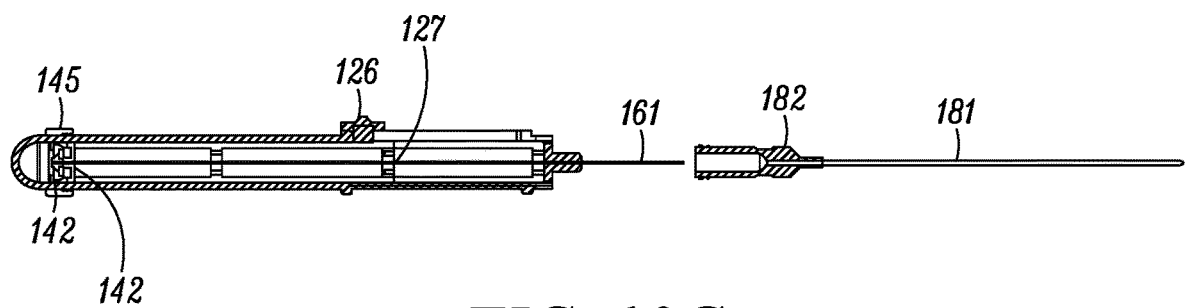

Another position of the catheter inserter 100 is shown in FIGS. 9G and 10G. The lock 145 is slid back to retract the needle 141 back into the housing 101. In an example, the lock 145 can be threaded onto the proximal threads 112 to fix needle assembly 140 in the housing 101. In another example, a mechanical device may automatically retract the needle assembly when the catheter assembly exits the distal end of the housing. For example, the mechanical means can be a spring that urges the needle assembly proximally. The spring can be released when the catheter assembly exits the housing. The spring can be a compression spring to retract the needle assembly back into the housing.

While not shown for purposes of clarity of illustration, it will be understood that the needle 141 can be covered by a cap (not shown) in the storage of the catheter inserter 100 before use. Such a cap can engage the housing distal end 105 to be removably fixed to the housing 101. This can help prevent accidental sticks with the needle and assist in keeping the needle 141 sterile.

The above embodiments describe having a needle, a guide wire and a catheter. It will be understood that the above embodiments also include examples where there is no guide wire. The actuator assembly engages the catheter and partially inserts the catheter into the patient's vasculature. However, the catheter may not be fully removed from the housing. The actuator assembly releases from the catheter, is retracted and then reengages the catheter. Now the actuator assembly can move the catheter forward. These steps may be repeated as needed until the catheter is outside the housing. The actuator assembly can now fully insert the catheter and eject same from the housing.

Figure 11:
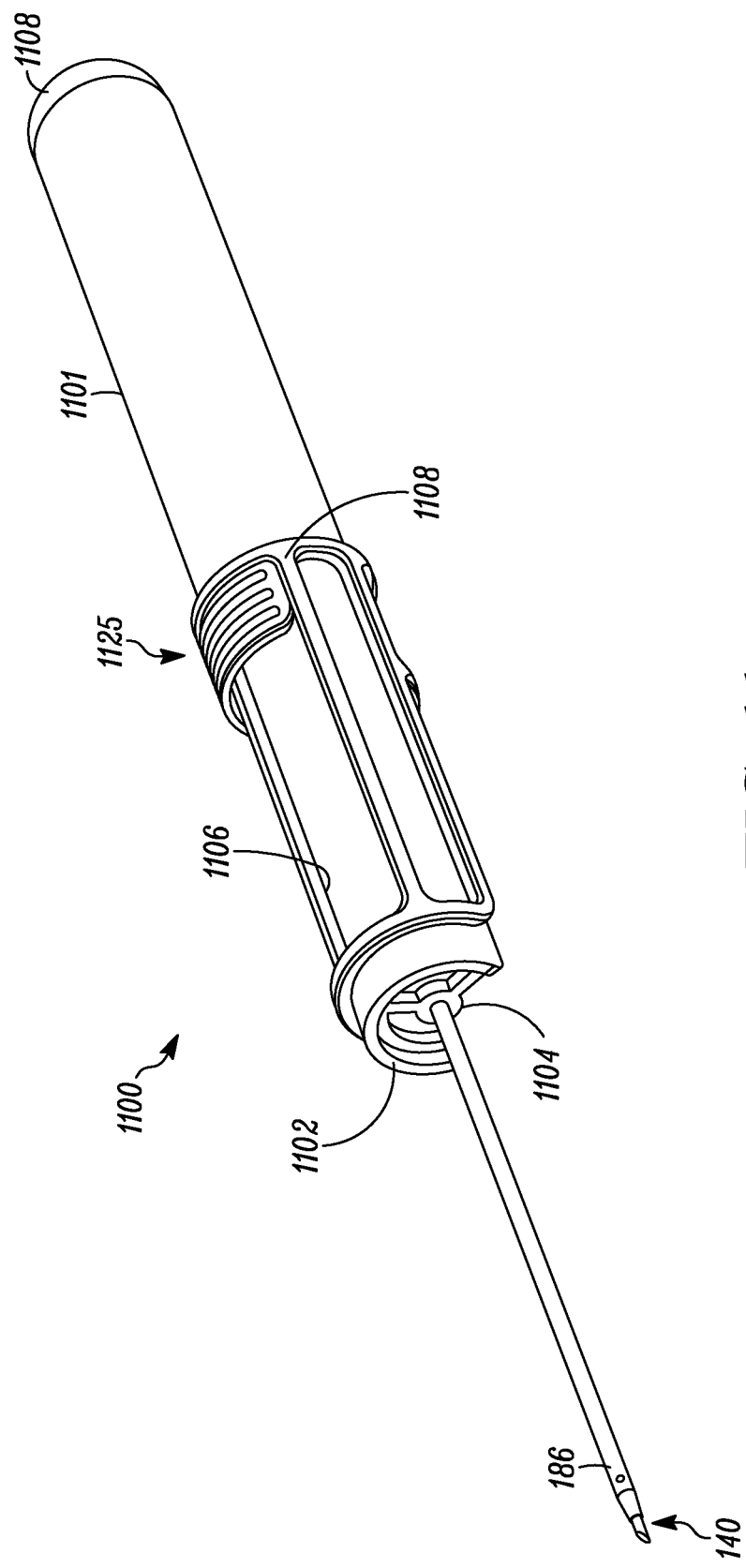
FIG. 11 is a perspective view of a catheter inserter in an example embodiment in an example embodiment.

FIG. 11 shows a perspective view of a catheter inserter 1100. This embodiment designates elements that are the same or similar to elements of the prior embodiment with the same reference number plus 1000. The catheter inserter 1100 operates to insert a catheter into the body of a patient, e.g., a human or animal. Catheter inserter 1100 includes a housing 1101 that is elongate and has a thin wall to define an open interior between a distal end 1102 and a proximal end 1103. The proximal end 1103 can be closed and integrally formed with the elongate, hollow body of the housing 1101. The distal end 1102 is open so that various components, e.g., the needle and/or catheter, can extend outside the housing. A seal 1105 is positioned on the distal end 1102. The seal 1105 can be frangible, in an example, to allow components to be pressed therethrough. The seal 1105 may include a slit extending along a diameter that allows small components to extend therethrough but not allow larger objects therethrough. Such larger objects (e.g., the catheter hub) may force the seal 1105 off the distal end 1102. The housing 1101 can include a flat portion 1104 adjacent the distal end 1102 and on the opposite side of the housing from the actuator 1126. A frame 1109 is positioned on the housing 1101 and around the housing. The frame 1109 can encompass the flat portion 1104 and define a slide track for the actuator 1126. The frame 1109 can include ribs that extend longitudinally along the sides of the housing and lateral webs that extend around the housing. Additional webs can be provided on the flat portion 1104 to provide additional grips for the user's hand. The frame 1109 can be adhered to the housing or integrally formed with the body of the housing 1101. The housing 1101 may be other shapes that are elongate and have an open interior to receive other components. The housing 1101 can be formed of a rigid polymer and portions thereof may be transparent. With the housing 1101 being transparent, the internal components in the housing 1101 of the catheter inserter 1100 can be viewed while operating. The housing 1101 is adapted to support an actuator assembly 1125 that selectively engages a catheter assembly 1180 to move these assemblies relative to the housing. The housing 1101 further supports a needle assembly 1140 in a fixed position to insert into the patient's body and a retracted position after the catheter is inserted into the patient's body. The housing 1101 includes a slot 1106 adjacent the distal end 1102 that aligns with the actuator assembly 1125 and allows the actuator assembly to be inside and outside the housing. A needle support 1108 is positioned at the distal end 1102. The support 1108 includes an aperture held by supports to support the needle when the device is in use. As a result the user need not use a second hand to support the needle 140, which tends to bend due to its length, narrow width and thin wall. In a use case, the catheter inserter 1100 can be used with one hand of the medical professional. The other hand of the medical professional can be free to engage the patient or perform other tasks, e.g. holding an ultrasound probe.

Figure 12A:
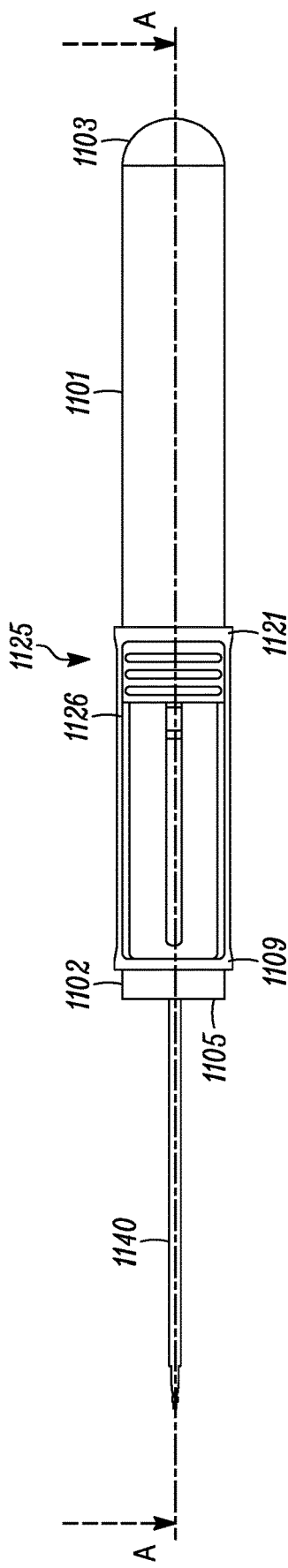
FIGS. 12A-12F show various views of the catheter inserter in an example embodiment.
Figure 12B:
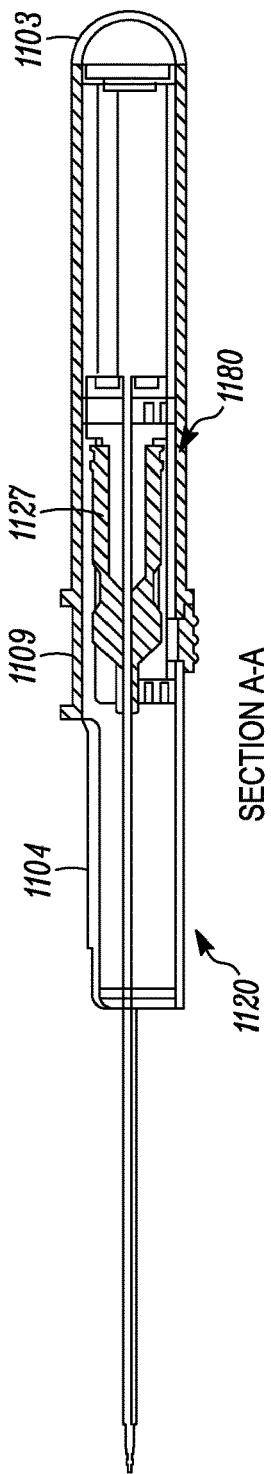
Figure 12C:
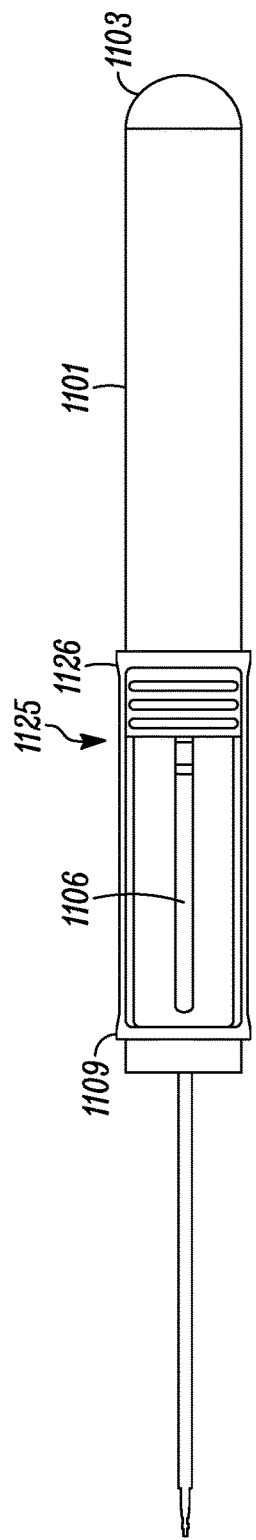
Figure 12D:
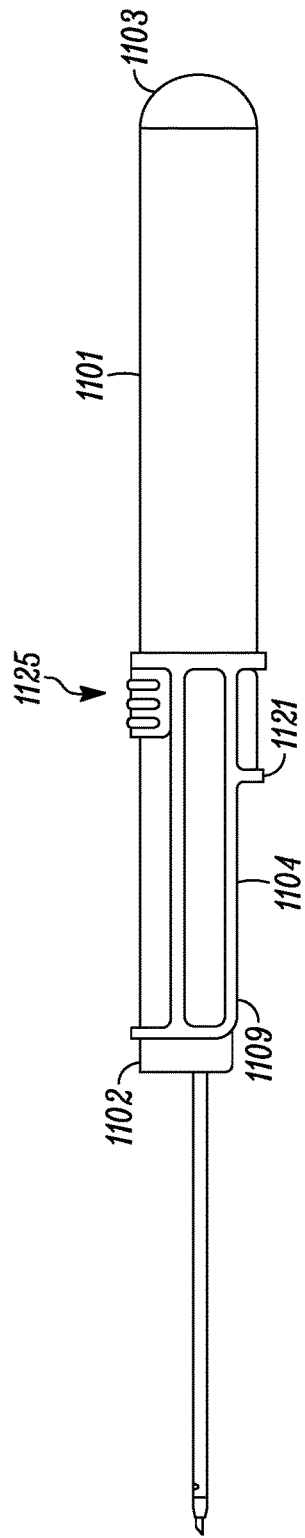
Figure 12E:
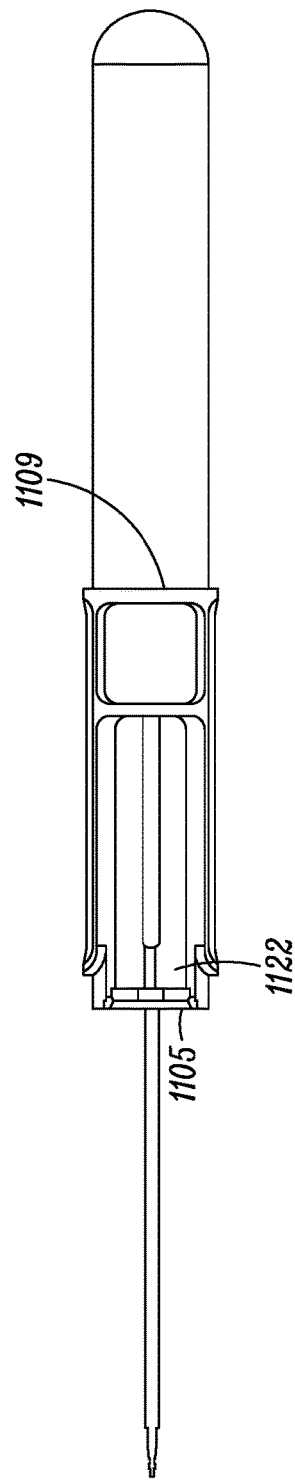
Figure 12F:
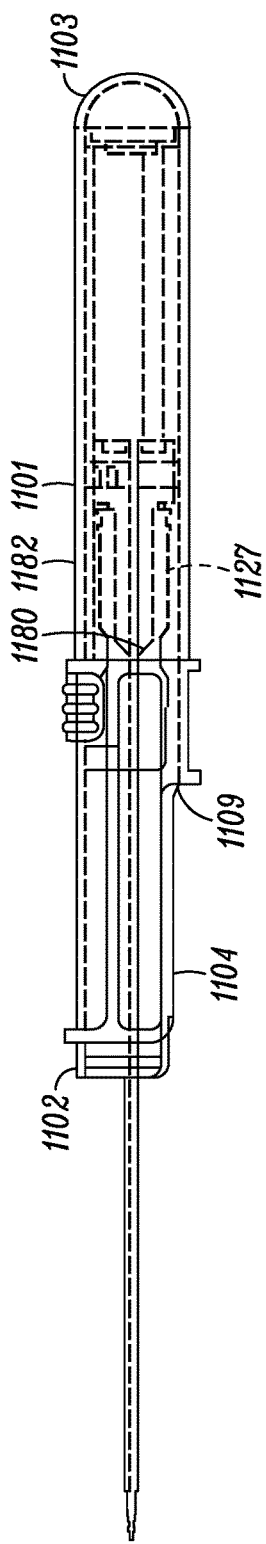
Figure 13:
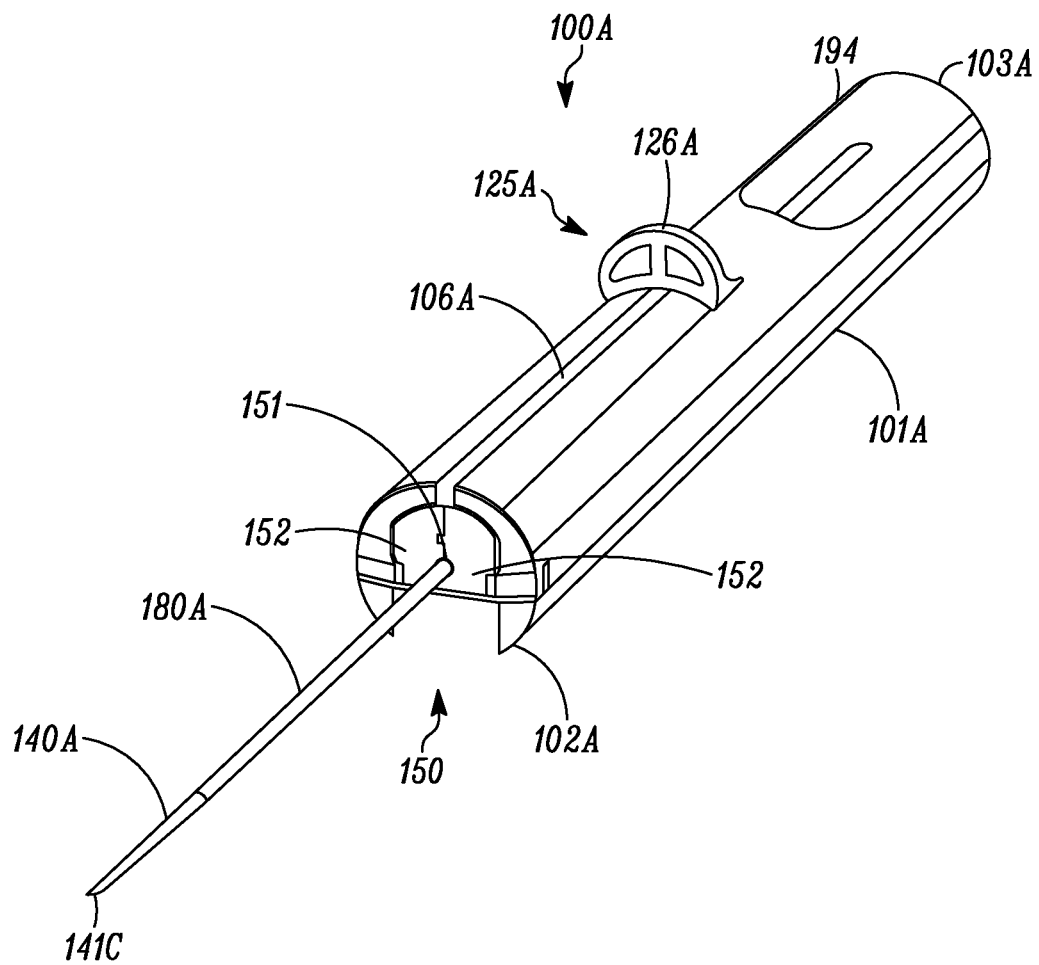
FIG. 13 shows a perspective view of a catheter inserter in an example embodiment.

The actuator assembly 1125 includes an actuator 1126 that is adapted to slide on or in alignment within the frame 1109 on a top surface of the housing 1101. In an example, the actuator 1126 has a width that is essentially the same as or slightly less than a slide part of the frame 1109. Actuator 1126 can include at least one upraised ridge extending away from the housing 1101 and providing an engagement surface for a user's thumb or finger. Actuator 1126 further includes a recess (not shown) in the bottom thereof. Actuator assembly 1125 further includes a shuttle 1127 (FIGS. 12B and 12F) with an outer diameter less than an inner diameter of the housing to allow the shuttle to travel in the longitudinal direction in the housing 1101. The shuttle 1127 includes a protuberance that extends upwardly from the body of the shuttle through the slot 1106 to be fixedly received in the recess of the actuator 1126 when assembled. The protuberance is positioned closer to the shuttle distal end than the shuttle proximal end. A user can engage the actuator 1126 and move the shuttle 1127 proximally and distally along the length of the slot 1106.

Housing 1101 can have an elongate slot to provide visual access into the interior of the housing 1101. The internal components, e.g., the actuator assembly internal parts, the catheter, the needle, etc., can be viewed through the slot. The slot also reduces weight and provides a contact portion for the user's hand to grip and guide the housing.

The needle assembly 1140 includes a needle with a distal end to insert into a patient and a proximal end that is fixed to a base. The base can be shaped to match the interior of the housing 1101 to allow the needle assembly 1140 to travel in the housing and have features as described above. Alternatively, the needle assembly 1140 is fixed to the housing and does not move. A needle cap can be provided to cover the sharp end of needle after use of the catheter inserter. The beveled part of the need end is fixed relative to the housing so that the beveled tip is at the same location. That is, the needle (and other components) do not rotate within the housing interior. However, a moving needle may be desirable when storing the catheter inserter 1100 or after using the assembly 1100, it is not typically desired during use.

In use, the user holds the housing 1101 in one hand with a digit, e.g., index finger or thumb, at the slide 1126. The needle 1140 is inserted into the vasculature of a patient. The user engages the slide 1126 and moves the slide forward along the slot 1106. The shuttle 1127 engages the catheter assembly and moves the catheter out of the distal end 1102 over the needle 1140. In some examples, the catheter is longer than the travel length of the actuator assembly. The user pulls the slide 1126 back toward the proximal end. The shuttle disengages from the catheter assembly and the catheter assembly stays in this intermediate position. When the actuator assembly is proximal, it reengages the catheter assembly. The user now slides the actuator assembly forward toward the distal end. The actuator assembly now moves the catheter assembly out the distal end and disengages from the catheter assembly. The housing and needle assembly are retracted proximally with the catheter assembly remaining with the patient.

The FIGS. 11 and 12 embodiments have material removed from the bottom of the housing relative to the FIG. 9 embodiments. This allows the catheter inserter 1100 to be used with a smaller angle of insertion relative the catheter inserter 100. The angle of insertion can be measured relative to either the longitudinal axis (or nearest surface of the needle to the patient's body) of the needle and the patient's body. The angle of insertion may also be measured relative to the housing. The needle may be co-axial with the housing about their longitudinal axes. This may make the inserter 1100 easier for the user to insert the needle into the vasculature of the patient. In an example, the angle of insertion is in a range of 3 degrees to 15 degrees, a range of 5 degrees to 10 degrees, or 6 degrees, +/−0.5 degrees.

With reference to FIG. 13-26, a catheter inserter 100A is shown, The catheter inserter 100A is configured to insert a catheter into the body of a patient, e.g., a human or animal. The catheter inserter 100A is similar to the inserter 100 described above. Similar parts are labeled with the same reference number with the suffix "A" added thereto. It will be understood that it is within the scope of the present disclosure to alter the features of catheter inserter 100A to include features of the catheter inserter 100, and vice versa. In an example, the catheter inserter 100A does not use a guide wire.

Catheter inserter 100A includes a housing 101A that is elongate and is at least partially hollow between a distal end 102A and a proximal end 103A. In general, the housing 101A can be cylindrical or a modified cylindrical shape. The housing 101A may have other external shapes, but must include an at least partly hollow interior. The housing 101A may be other shapes that are elongate and have an open interior to receive other components. The proximal end 103A can be closed and integrally formed with the elongate, hollow body of the housing. The distal end 102A is open so that various components can extend outside the housing. The housing 101A can be formed of a rigid polymer and portions thereof may be transparent. With the housing 101A being transparent, the internal components in the housing 101A of the catheter inserter 100A can be viewed while operating. The housing 101A is adapted to support an actuator assembly 125A that selectively engages a catheter assembly 180A to move these assemblies relative to the housing. The housing 101A further supports a needle assembly 140A in a fixed insertion position to insert the needle 140A into the patient's body and an after use position after the catheter is inserted into the patient's body. In an example, the after-use position includes covering the needle tip to increase the level of safety.

The housing 101A includes a slot 106A adjacent the distal end 102A that aligns with the actuator assembly 125A and allows the actuator assembly to be inside and outside the housing 101A. The slot 106A is open at the distal end and closed at the proximal end. The open distal end of the slot 106A allows the actuator assembly 125A to have components that exit the housing to insert the catheter 180A into the patient.

Figure 20:
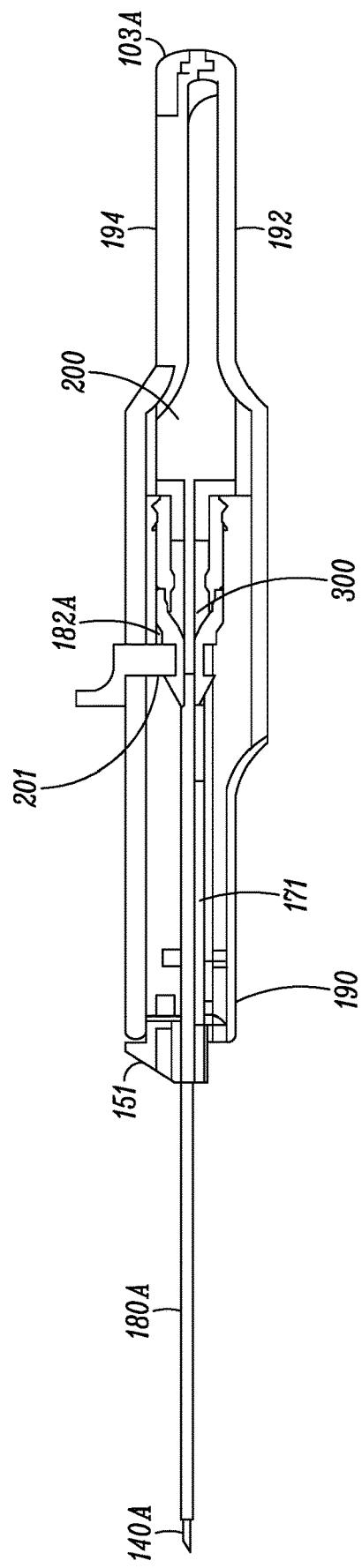
FIG. 20 shows a vertical cross section view taken along longitudinal center of the catheter inserter.
Figure 21:
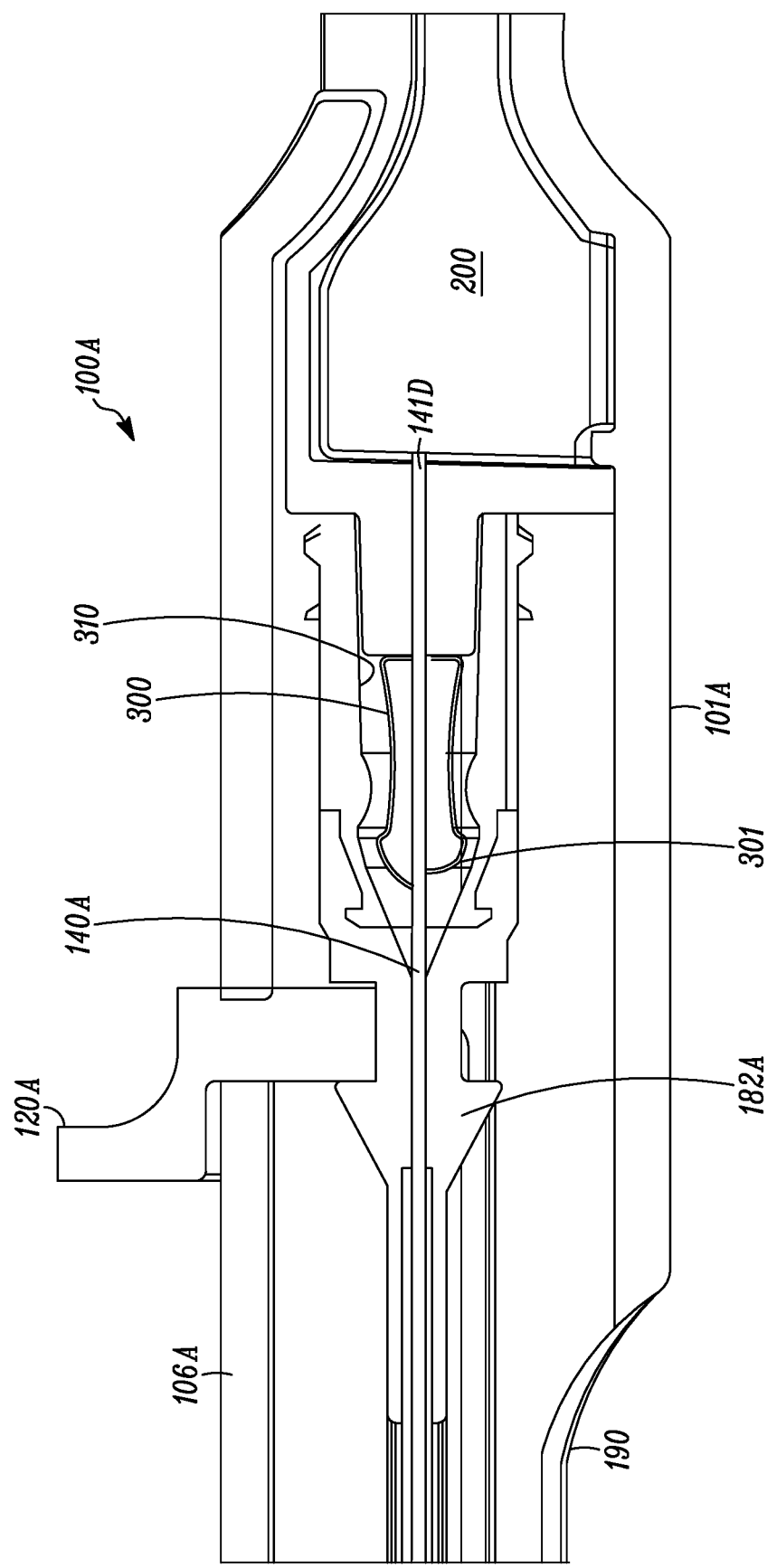
FIG. 21 shows an enlarged view of the center of the FIG. 20 catheter inserter.
Figure 22:
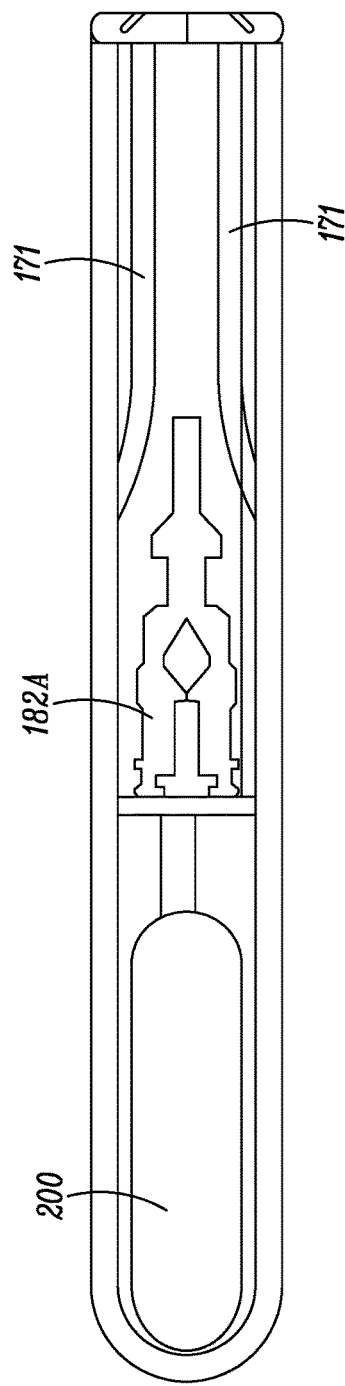
FIG. 22 is a horizontal cross section taken along the longitudinal center of the catheter inserter.

The housing 101A includes a recess 190 at the distal end 102A (FIGS. 15, 20 and 21). The recess 190 can be a true recess with a portion of the housing body removed so that the distal part of the housing is open to the interior from the bottom of the housing. The recess 190 may also be a closed, if it can provide enough room for the catheter hub 182A to pass through the housing at the distal end 102A. The recess 190 at the distal end of the catheter inserter 100A is configured to achieve a shallow angle relative to the patient's body versus a device without the recess 190. In an example, the angle of the catheter inserter 100A relative to the patient can be reduced by about 10 degrees or fewer, 7 degrees or fewer, 5 degrees or fewer, or about 2.0 degrees, depending on the length of the needle, the length of the housing 101A and the length of the recess 190. The recess 190 may be defined by a chord across the housing 101A, when the housing is generally cylindrical. The chord will be positioned below the diameter of the housing 101A. In an example, the chord defining the cut surface of the housing forming the recess is about one-quarter of the height of the housing 101A.

The housing 101A at the proximal end 103A may have a recessed part 192 on the bottom of the housing (FIGS. 15 and 20). The housing may be cylindrical only at the middle portion 193 of the housing. Before use, the catheter hub 182A is positioned in the middle part 193 of the housing.

The housing 101A at the proximal end 103A includes a flash chamber 200 positioned in the proximal interior part of the housing. The housing part 194 above the flash chamber 200 can be planar with a viewing window 195 therein. In an example, the flat housing part 194 is defined by a chord above the center diameter of a cylindrical housing. The viewing window 195 can be elongate and relatively thin in width, e.g., greater than ten times longer than wide. The flash chamber 200 is in fluid communication with the proximal end of the needle such that bodily fluids may flow into the flash chamber 200 when the needle is inserted into a patient's body.

In a use case, the catheter inserter 100A can be used with one hand of the medical professional. The other hand of the medical professional can be free to engage the patient or perform other tasks, e.g. holding an ultrasound probe. The needle 140A is fixed in position relative to the housing 101A. The housing 101A can be gripped by the user intermediate the distal end 102A and the proximal end 103A. The user can engage the actuator assembly 125A, e.g., using a thumb or other finger, to move the catheter assembly 180A distally toward the free end of needle 140. The catheter assembly 180A can move out of the housing 101A through the distal end 102A.

Figure 14:
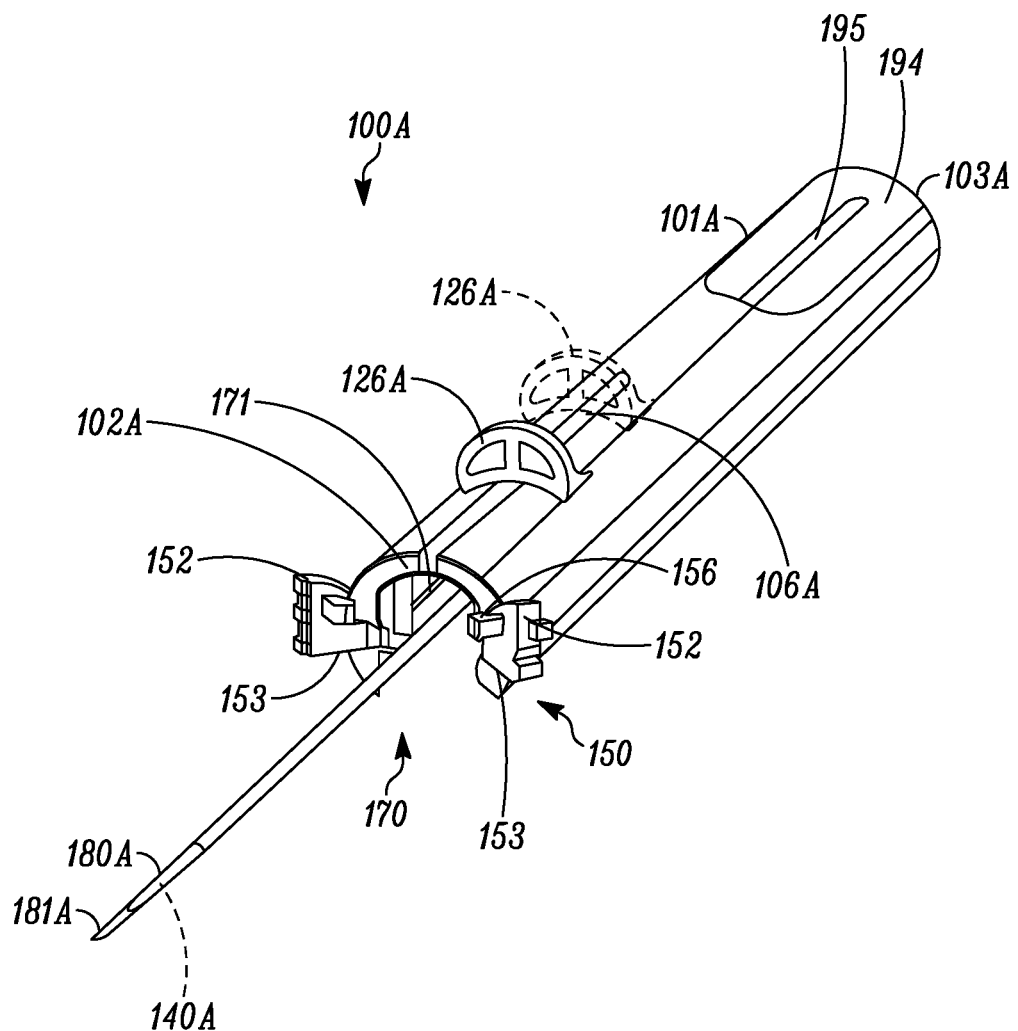
FIG. 14 shows a perspective view of a catheter inserter, in a second position, in an example embodiment.

The distal end 102A of the housing 101A is closed by a door assembly 150 (FIGS. 13, 14, and 17-19). In the closed position, access to the interior of the housing 101A through the distal end 102A is blocked. The door assembly 150 can open to allow the catheter assembly 180A to pass through the distal end 102A (FIG. 14). The actuator assembly 125A moves from a proximal position (FIG. 13) to a distal position (FIG. 14) to move the catheter assembly through the door assembly 150.

The door assembly 150 supports the needle 140A intermediate its two ends, the distal end 141C and the proximal end 141D. The needle 140A and the catheter 180A extend through the aperture 151. In an example, an aperture 151 is formed in the door assembly 150 through which the needle 140A extends. The needle 140A may require this intermediate support do its tendency to bend during its use. This is an inherent property of most needles as they have a small diameter and a thin wall relative to their length. In some instances the door assembly 150 supports the needle generally at the mid-length thereof, or within 10% or 20% of the mid-length.

Figure 17:
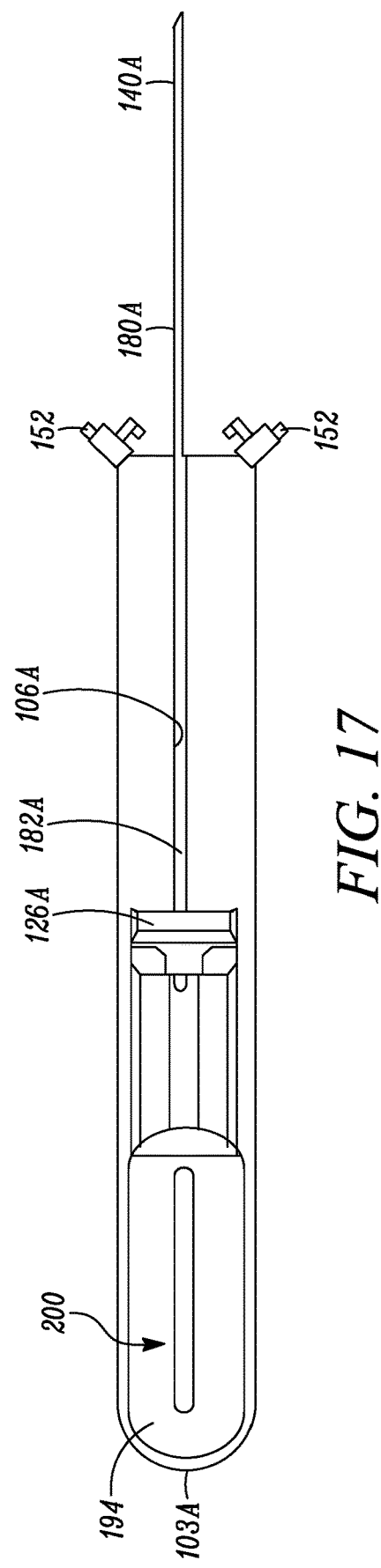
FIG. 17 shows a side elevational view of a catheter inserter, in a second position, in an example embodiment.

The door assembly 150 includes at least two doors 152 that are connected to the body of the housing 101A at the distal end 102A. A hinge 153 connects a door 152 to the housing 101A and allows the door to move from a closed position (FIGS. 13 and 16) to an open position (FIGS. 14 and 17). The aperture 151 may be formed along the seam between the doors 152.

Figure 18:
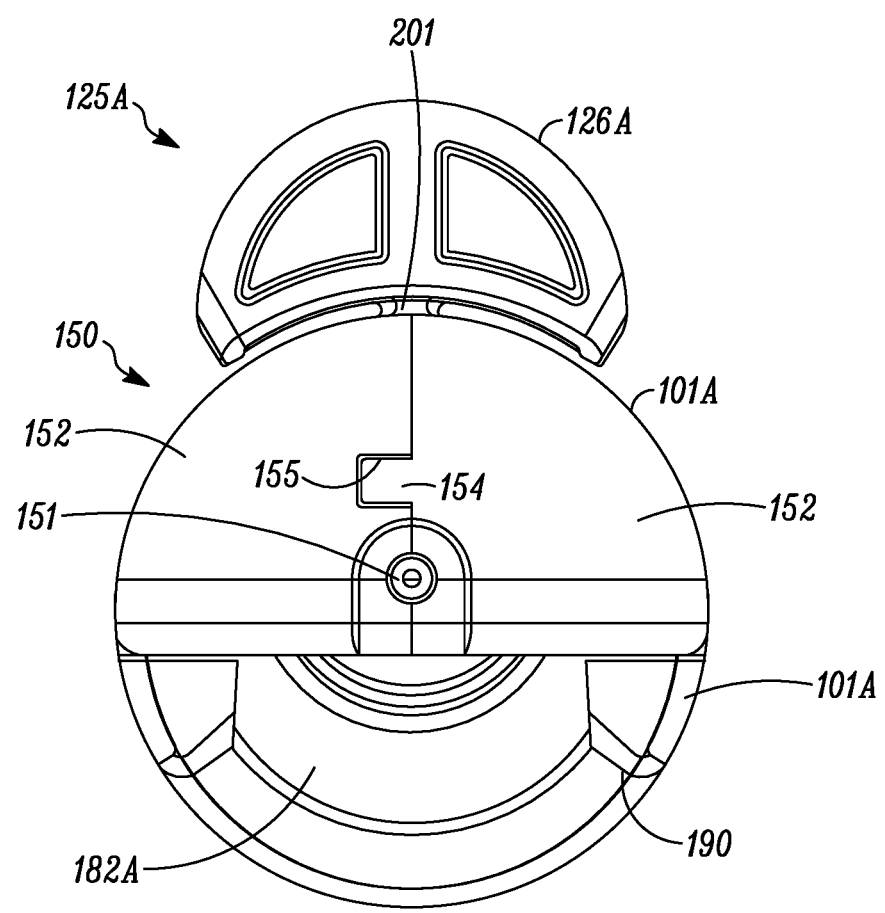
FIG. 18 shows an end view of a catheter inserter in an example embodiment.
Figure 19:
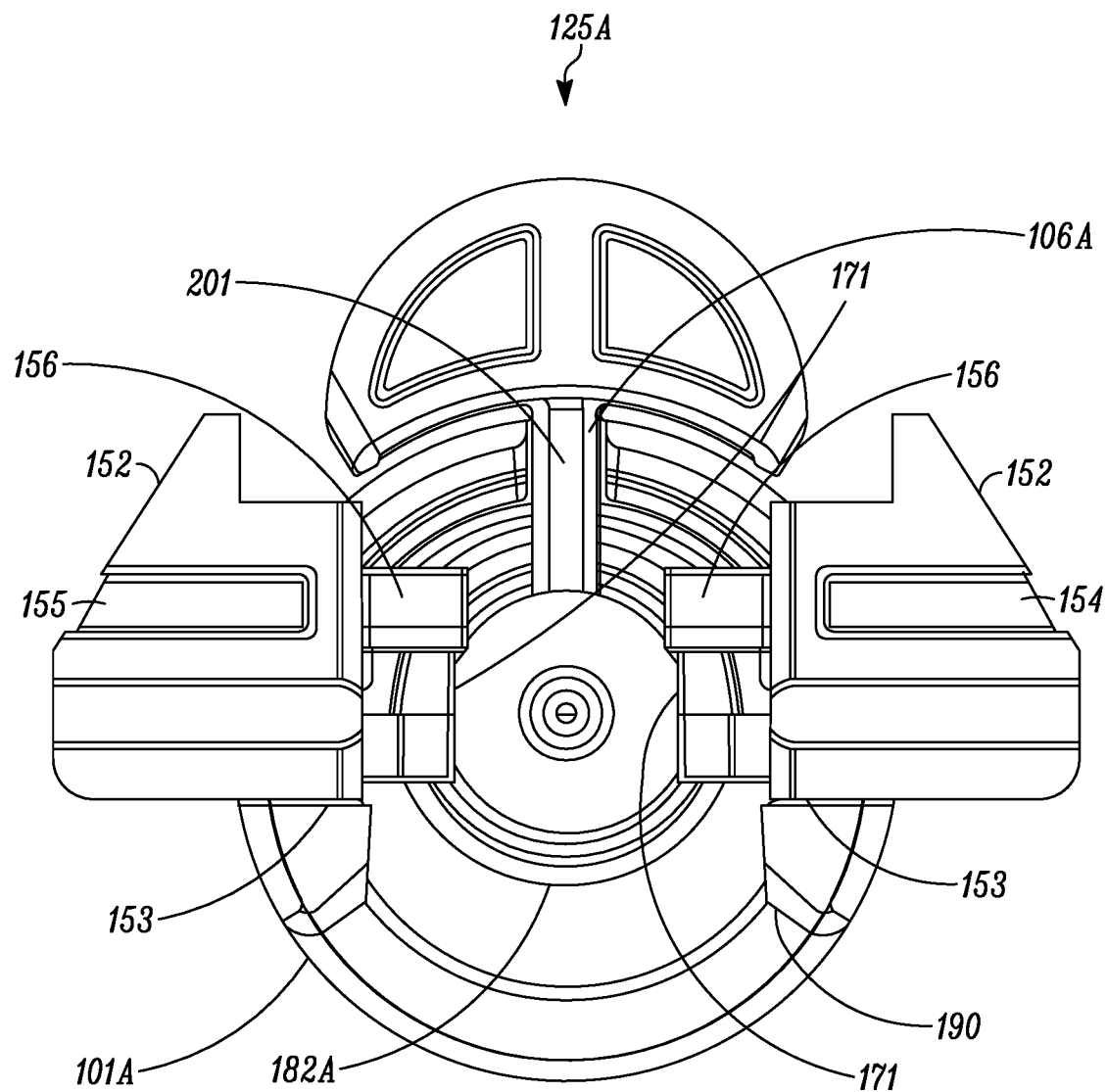
FIG. 19 shows an end view of a catheter inserter, in a second position, in an example embodiment.

The doors 152 may include mating structures to assist in holding the doors together (FIG. 18-19). The mating structure can have male and female parts that interconnect when the doors are closed. The mating structures include a protrusion 154 that is configured to fit in a recess 155 of another door. The protrusion 154 can be an elongate polygonal structure that fits into a recess 155 that is essentially the inverse of the protrusion 154. The mating structure is a slide fit that does not interfere with the opening of the doors 152 as described herein. The mating structure may add structure, e.g., mechanical, integrity to the inserter 100A when the doors 152 are closed.

The actuator assembly 125A includes an actuator 126A that is engagable by a user at a part thereof that extends outside the housing 101A. The actuator 126A extends through the slot 106A and releasably connects to a catheter hub. The catheter hub connects to the proximal end of the catheter within the interior of the housing 101A. When the actuator 126A moves from the proximal position (FIG. 13) to the distal position (FIG. 14) toward the housing distal end 102A, the catheter hub moves toward the housing distal end 102A. The catheter hub may contact the doors 152 to drive the doors open. During this movement, the needle 140A is held in place and the catheter 180A slides along the needle into a vessel of the patient, driven by the actuator 126 driving the catheter hub distally.

Optionally, a seal (not shown in FIG. 13) can be positioned on the distal end 102A. The seal can be frangible, in an example, to allow components to be pressed therethrough. The seal may include a slit extending along a diameter that allows small components to extend therethrough but not allow larger objects therethrough. The seal may be similar to the seal 105. Such larger objects may force the seal off the distal end 102A. In an example, the doors 152 may force the seal off the distal end 102A.

Optionally, the housing 101A may have a flat portion whereat the actuator 126A travels. This may allow the actuator 126A to move freely on the housing and simplify construction of the actuator.

The actuator assembly 125A further includes a latch mechanism 170 mounted to the housing 101A, e.g., within the housing interior. The latch mechanism 170 holds the doors 152 in the closed position (FIG. 13) until the actuator 126a is moved forward toward the housing distal end 102A. In an example, the catheter hub or the actuator 126A contacts or actuates the latch mechanism 170 to release the doors 152.

Figure 23:
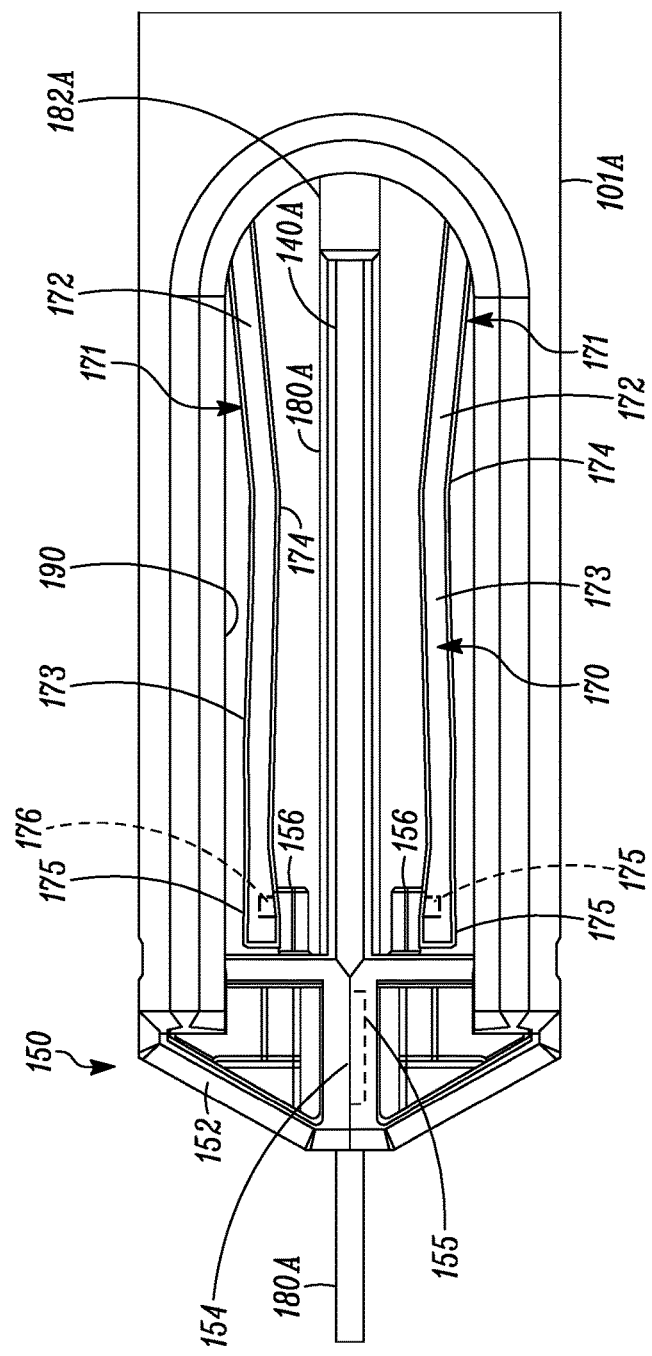
FIG. 23 shows an enlarged view of the distal end of the bottom of the catheter inserter.
Figure 24:
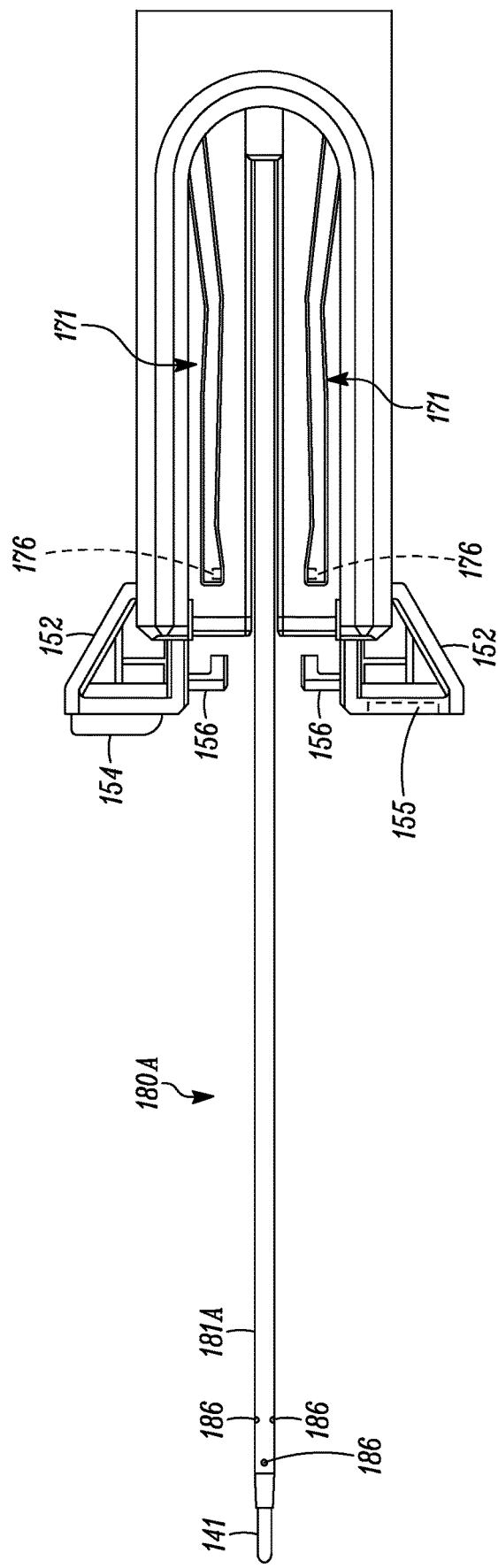
FIG. 24 shows an enlarged view of the distal end of the bottom of the catheter inserter.

FIGS. 23 and 24 show an enlarged view of the door assembly 150 and the latch mechanism 170 at the distal end 102A of the housing. The doors 152 are closed in FIG. 23. The doors 152 are open in FIG. 24. The latch mechanism 170 includes two control arms 171 that are cantilevered to the housing 101A with the proximal end of the arm being fixed to the housing. The distal end of the arms 171 are the free ends. The control arm 171 includes an upper arm 172 and a forearm 173 joined by an elbow 174. The upper arm 172 is fixed to the housing 101A and extends at a first angle, which can be in a range of 3 degrees to 15 degrees, a range of 5 degrees to 10 degrees, or 6 degrees, +/−0.5 degrees. At least part of the upper arm 172 extends into the travel path of the catheter hub. At the elbow 174, the angle of the arm 171 changes to a lesser angle. As a result the forearm 173 extends essentially parallel to the inner surface of the housing 101A. The forearm 173 is spaced inwardly into the interior space of the housing. The forearm 173 is positioned to be in the travel path of the catheter hub 182A. In an example, the arm 171 is made of a material than bends out of the way of the collect hub 182A under the motive force from the user's finger through the actuator assembly 125A. The free end 175 of the arm 171 includes a connection to the door 152. In an example, the connection is a catch 176. The catch 176 can include a recess. The door 152 includes a latch 156 that is configured to be received in the catch 176. A detent structure may assist in holding the latch 156 in the catch 176. With the latch 156 in the catch 176, the doors 152 are held closed. The forearm 173 is urged toward the center of the housing. The arm 171 holds the latch 156 so that the doors 152 are in the closed position as shown in FIG. 23. In this position, a user may hold the housing and insert the needle into a patient, e.g., into a vessel. This can be done with a single hand. Once the user has inserted the needle, then it is desired to release the doors 152 to the open position. It is desired to move the arms 171 outwardly toward the wall of the housing 101A. When the arms 171 are moved outwardly, the latch 156 is released from the catch 176. The doors 152 can swing freely on the hinges 153. In another example, the doors 152 may be completely released from housing 101A when the latch 156 is released from the catch 176. In an example, the movement of the catheter hub 182A toward the distal end 102A causes the catheter hub 182A to engage the control arms 171. Initial contact may be on the upper arm 172 before the elbow 174. Continued movement of the catheter hub 182A on the arm will force the arm radially outwardly in the housing 101A. When the control arm 171 moves outwardly at a distance greater than the height of the part of the latch 156 in the catch 176, the doors 152 will be released from the control arms 171. The catheter hub 182A is now free to travel out of the housing distal end 102A, which is now open.

The actuator 126A is releasably connected to the catheter hub 182A through the linkage 201. The linkage 201 connects to hub, e.g., using a bayonet connection or press fit. When the catheter hub 192A is free from the housing 101A, then the linkage 201, along with the actuator 126A can be removed from the catheter hub 182A. The catheter hub 182A can be then used as a catheter hub and connect to other medical equipment, e.g., by threads on the hub, a snap fit, a luer connector, or other connector. The linkage 201 may include a yoke that extends around the catheter hub hub 182A in an annular ring.

The end of the catheter 181, 181A can be fenestrated and include a plurality of apertures 186 (see e.g., FIG. 24). The apertures 186 (e.g., fenestra) are spaced around the circumference of the catheter end. In an example, the apertures 186 are evenly spaced around the circumference. The apertures 186 can direct some of the fluid being sent through the catheter 181, 181A radially outwardly. By evenly spacing the apertures 186, the fluid flowing out of the apertures 186 will assist in holding the catheter end in the middle of the patient's vessel. This may reduce undesirable effects when the catheter end contacts the vessel wall.

A needle safety clip 300 may be mounted to the proximal end of the catheter hub 182A (FIGS. 20 and 21). The safety clip 300 is releasably mounted in a recess 310 in the proximal end of the catheter hub 182A. When the catheter hub 182A travels toward the distal end 102A, and exits the housing, the clip 300 travels therewith. The needle 140A may have a structure, e.g., a protrusion or other raised surface, which travels within the catheter 180A and engages the needle safety clip 300. The needle safety clip includes a moveable end 301 that closes after the needle moved there past. The engaging structure will prevent the needle from passing all of the way through the needle safety clip 300. Thus, the clip is released from the recess 310 and remains on the end of the needle 140A. Examples of safety clips include devices shown in U.S. Pat. Nos. 5,053,017; 5,135,504; 5,344,408; 5,584,809; 6,616,630 and 6,749,588, which are hereby incorporated by reference for any purpose.

Figure 25:
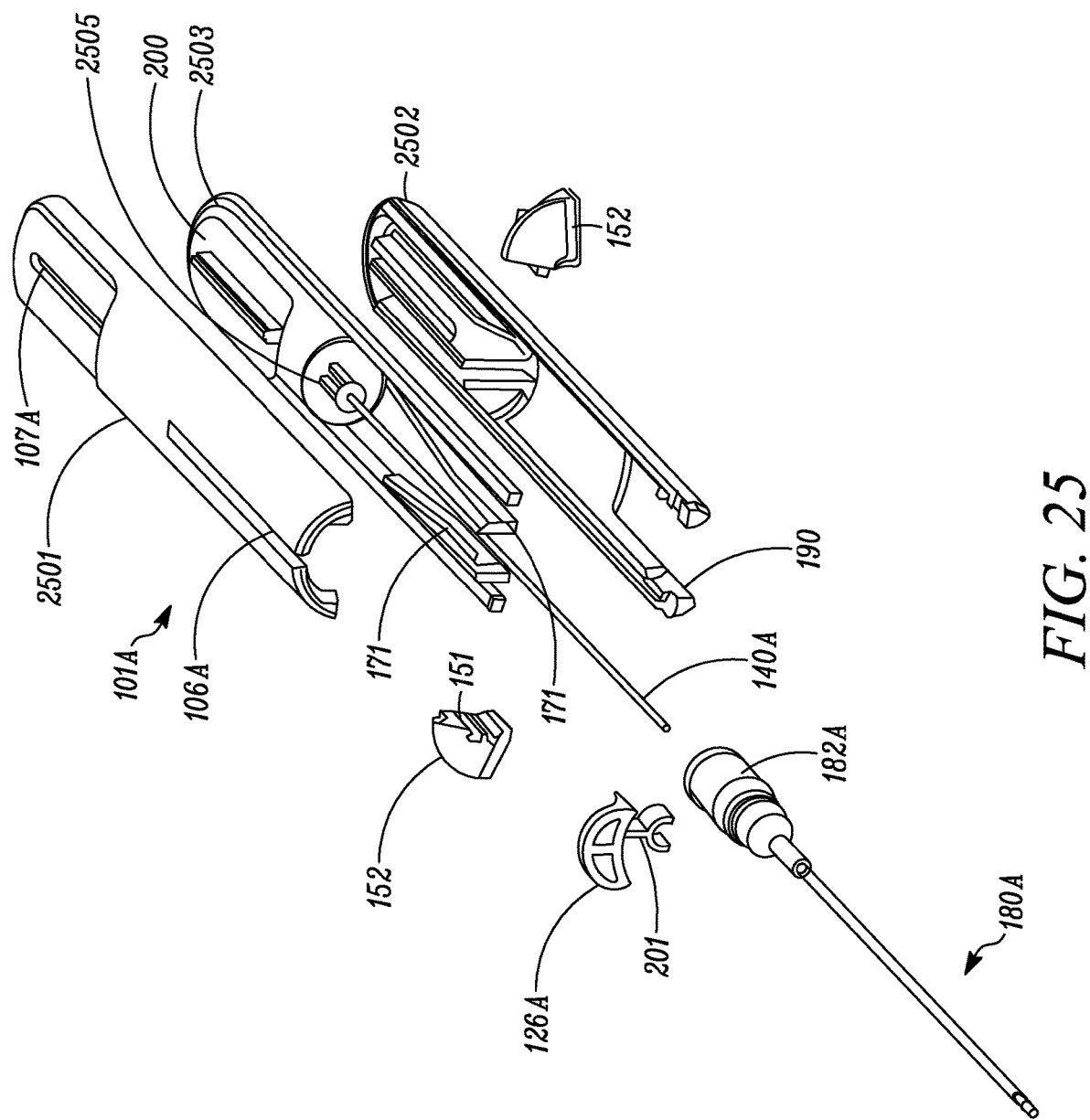
FIG. 25 shows an exploded view of the catheter inserter.
Figure 26:
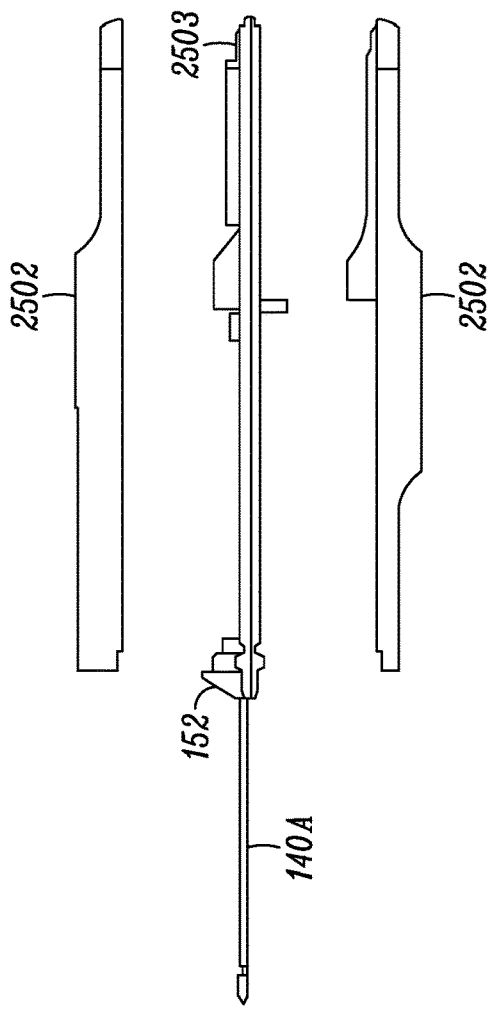
FIG. 26 shows an exploded second view of the catheter inserter.
Figure 26:
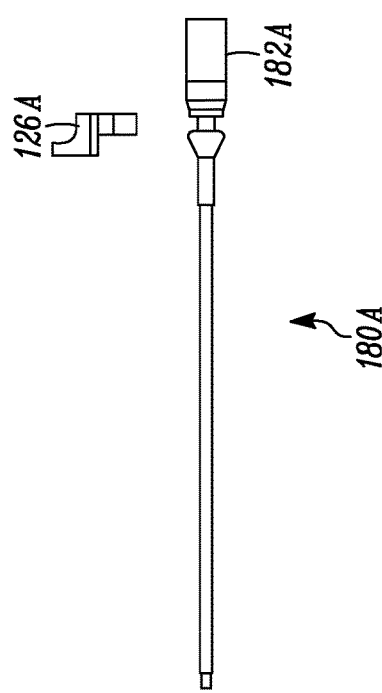

FIGS. 25 and 26 show exploded views of the catheter inserter 100A. The housing 101A is formed of three parts, an upper housing part 2501, a lower housing part 2502 and a middle housing part 2503 that is positioned between the upper housing part 2501 and the lower housing part 2502. The upper housing part 2501 can be fixed to the lower housing part 2502, e.g., by an adhesive or through other mechanical means. The outer periphery of the upper, lower and middle housing parts 2501, 2502, and 2503 may have alignment structures, e.g., ridges, recesses, guides, pins, detents, and the like, so that the housing parts align properly and are fixed together. The slot 106A and slot 107A are formed in the upper housing part 2501. The lower housing part 2502 has the recess 190 formed in therein. The lower housing part 2502 is configured to be adjacent the patient's body when the needle is inserted. The lower housing part may include supports that extend upwardly and may be on the outside of the needle securing structure 2505 of the middle housing part 2503. The needle securing structure 2505 fixes the needle in the middle housing part 2503 and allows fluid communication with the flash chamber 200 so that bodily fluids may travel through the needle to flash chamber 200. An upper extension of the flash chamber is transparent and extends into the slot 107A so that the contents of the flash chamber 200 can be viewed. The middle housing part 2505 includes outer arms that extend parallel to or define part the outer wall of the housing 101A. The control arms 171 are fixed to the proximal part or an intermediate part of the outer arms. The control arms 171 are cantilevered from the outer arms and then extend radially inwardly and in the longitudinal direction of the outer arms.

The presently described examples of the catheter inserter may be operated by a single hand of the medical professional, leaving the other hand free for other tasks. The catheter inserter further operates to insert, into a patient, a catheter. The medical professional may use their other hand to operate other medical equipment, e.g., an ultrasound probe. The presently described catheter inserter provides a method for inserting a catheter (e.g., a midline catheter) over a needle with the needle inserted while an ultrasonic probe is being held by the same medical professional. The ultrasound display may be placed close to the patient so that the medical professional can easily see the needle insertion point, the needle, the ultrasound probe and the ultrasound display. The medical professional can simultaneously manipulate the ultrasound the ultrasound probe and the catheter inserter, including needle insertion and sliding the catheter over the inserted needle.

In an example, the catheter may have a length greater than the range of movement of the operator's finger or thumb. The catheter may be greater than 1.5 inches in length, greater than 3 inches in length, greater than 5 inches in length, greater than 6 inches in length. In an example, the catheter is in the range of 3.0 to 6.0 inches in length. The catheter inserter may include an actuator assembly that engages the catheter multiple times to move the catheter from the housing into the patient's vasculature. In an example, the travel distance of the actuator assembly is about 1.0 inch to about 1.5 inch. Thus, in the case of a catheter of about 3.0 inches or less, the actuator engages the catheter twice to complete the process of inserting the catheter. Here the user must move the actuator toward the patient twice to fully insert the catheter. In the case of a 6 inch catheter, the actuator engages the catheter at least four times to complete the process of inserting the catheter. Here the user must move the actuator toward the patient four times to fully insert the catheter.

In an example, the catheter inserter may support the needle intermediate its length and after the needle is inserted, allow the catheter to move outwardly on needle into the patient. The catheter hub is released from the catheter inserter. The needle can be withdrawn from the patient while the released catheter with hub remains with the patient. In an example, doors are opened automatically by action of structures in the housing. The user's finger may provide the motive force. In an example, only a single hand is needed to guide the needle for insertion and also actuate the release of the catheter hub while moving the catheter into position on the patient.

The present catheter inserter, in some embodiments, is designed for inserting a midline catheter, e.g., measuring 8 inches or less with the distal tip dwelling in the basilic, cephalic, or brachial vein, at or below the level of the axilla, and distal to the shoulder.

The terms "distal" and "proximal" are with reference to the usual position of the medical professional who operates the catheter inserter 100 and not to the patient receiving the catheter.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A catheter inserter comprising:
   a housing having an outer wall, an open interior, and a distal open end;
   a needle assembly mounted in the open interior of the housing and to provide access through a patient's skin to a patient's vasculature, the needle assembly including a needle and a lock secured to the needle and slidable with the needle relative to the housing for selectively sliding the needle to a first, use position and a second, retracted position to fix the needle assembly in the first, use position and the second, retracted position;
   a catheter assembly removably positioned in the housing and including a catheter and a hub connected to the catheter; and
   an actuator assembly to move the catheter assembly to move the catheter and the hub outside the housing by engaging the catheter assembly,
   wherein the lock includes a locking ring on an outside of the housing, wherein the housing includes threads at a first housing position and at a second housing position axially spaced on the housing from the first housing position, and wherein the locking ring threadingly engages the threads at either the first, use position or the second, retracted position to position the needle of the needle assembly at either the first, use position or the second, retracted position.

2. A catheter inserter comprising:
   a housing having an outer wall, an open interior, and a distal end;
   a needle assembly mounted in the open interior of the housing and to provide access through a patient's skin to a patient's vasculature, the needle assembly including a needle that is slidably mounted relative to the housing between a first, use position and a second, retracted position within the housing;
   a catheter assembly removably positioned in the housing and including a catheter and a hub connected to the catheter;
   an actuator assembly to move the catheter assembly to move the catheter and the hub outside the housing by engaging the catheter assembly; and
   a lock that is movable relative to the housing to fix the needle assembly in at least one of the first, use position and the second, retracted position, wherein the lock includes an annular locking ring that extends about an entire outer circumference of the housing and is slidable relative to the housing.

3. The catheter inserter of claim 2 wherein the needle assembly includes a radially-extending protuberance, and wherein the housing includes a slot that receives the radially-extending protuberance for guiding axial movement of the needle relative to the housing.

4. The catheter inserter of claim 2 wherein the lock includes a lock thread that is threadably engageable with a first thread on an exterior of the housing, and is slidable along the exterior of the housing to a second thread on the exterior of the housing that is axially spaced from the first thread.

5. A catheter inserter comprising:
   a housing having an outer wall, an open interior, a distal end, and a door assembly that is pivotable between a closed position and an open position to selectively close at least a portion of the distal end;
   a needle assembly mounted in the open interior of the housing and to provide access through a patient's skin to a patient's vasculature, the needle assembly including a needle supported by the door assembly with the door assembly in the closed position;
   a catheter assembly removably positioned in the housing and including a catheter and a hub connected to the catheter; and
   an actuator assembly to move the catheter assembly to move the catheter and the hub outside the housing by engaging the catheter assembly,
   wherein the actuator assembly is configured to release the catheter assembly and to re-engage the catheter assembly within the open interior of the housing to move the catheter of the catheter assembly distally through the door assembly.

6. The catheter inserter of claim 5, wherein the actuator assembly includes an actuator connected to the hub; and wherein the hub engages a latch mechanism to open the door assembly to allow the catheter assembly to move outside the housing.

7. The catheter inserter of claim 6, wherein the door assembly includes at least one first door held in the closed position by the latch mechanism and at least one second door.

8. The catheter inserter of claim 7, wherein the at least one first door includes a latch, wherein the latch mechanism includes a control arm with a catch to receive the latch, the control arm is moved to release the latch from the catch with the hub engaging the control arm.

9. The catheter inserter of claim 7, wherein the at least one first door and the at least one second door matingly engage when closed and support the needle at the distal end of the housing when closed.

10. The catheter inserter of claim 9, wherein the at least one first door includes a protrusion and the at least one second door includes a recess to receive the protrusion with the at least one first door and the at least one second door being in the closed position.

11. The catheter inserter of claim 7, wherein the at least one first door includes an aperture to support the needle with the needle extending past the door assembly.

12. The catheter inserter of claim 7, wherein the at least one first door and the at least one second door form an aperture through which the needle of the needle assembly and the catheter of the catheter assembly extend with the doors in the closed position.

13. The catheter inserter of claim 7, wherein the at least one first door and the at least one second door cover more than half of the distal end of the housing while in the closed position.

14. The catheter of claim 5 wherein the door assembly is axially fixed and hingedly connected to the housing.

15. The catheter of claim 5 wherein the door assembly includes a first pivotable door and a second pivotable door that matingly engages the first door when in the closed position and is pivotable away from the first door when in the open position.

* * * * *

UNITED STATES PATENT AND TRADEMARK OFFICE
CERTIFICATE OF CORRECTION

| | | |
|---|---|---|
| PATENT NO. | : 11,471,648 B2 | |
| APPLICATION NO. | : 15/571168 | |
| DATED | : October 18, 2022 | |
| INVENTOR(S) | : Justin Hulvershorn et al. | |

It is certified that error appears in the above-identified patent and that said Letters Patent is hereby corrected as shown below:

In the Claims

In Column 19, Claim 14, Line 1, delete "catheter" and insert -- catheter inserter --, therefor.

In Column 19, Claim 15, Line 1, delete "catheter" and insert -- catheter inserter --, therefor.

Signed and Sealed this
Twenty-seventh Day of December, 2022

*Katherine Kelly Vidal*

Katherine Kelly Vidal
*Director of the United States Patent and Trademark Office*